(12) United States Patent
Kim et al.

(10) Patent No.: US 8,771,195 B2
(45) Date of Patent: Jul. 8, 2014

(54) CARDIOVASCULAR ANALYZER

(75) Inventors: Kwang Tae Kim, Seoul (KR); Seog San Hyeon, Seoul (KR)

(73) Assignee: Irumedi Co., Ltd. (KR)

( * ) Notice: Subject to any disclaimer, the term of this patent is extended or adjusted under 35 U.S.C. 154(b) by 565 days.

(21) Appl. No.: 13/121,692

(22) PCT Filed: Sep. 30, 2009

(86) PCT No.: PCT/KR2009/005625
§ 371 (c)(1),
(2), (4) Date: Mar. 30, 2011

(87) PCT Pub. No.: WO2010/038993
PCT Pub. Date: Apr. 8, 2010

(65) Prior Publication Data
US 2011/0172505 A1    Jul. 14, 2011

(30) Foreign Application Priority Data

Oct. 1, 2008    (KR) .................. 10-2008-0096524

(51) Int. Cl.
*A61B 5/02*    (2006.01)

(52) U.S. Cl.
USPC ........... 600/481; 600/485; 600/504; 600/508; 600/509; 600/528

(58) Field of Classification Search
None
See application file for complete search history.

(56) References Cited

U.S. PATENT DOCUMENTS

| | | | | |
|---|---|---|---|---|
| 5,265,011 A | * | 11/1993 | O'Rourke | 600/485 |
| 5,289,823 A | * | 3/1994 | Eckerle | 600/492 |
| 6,328,698 B1 | | 12/2001 | Matsumoto | |
| 7,174,203 B2 | | 2/2007 | Arand et al. | |

FOREIGN PATENT DOCUMENTS

| | | |
|---|---|---|
| JP | 2008-520340 | 6/2008 |
| KR | 10-2006-0078207 | 7/2006 |
| KR | 10-2008-0030189 | 4/2008 |
| WO | 95/16391 | 6/1995 |

* cited by examiner

*Primary Examiner* — Michael Kahelin
*Assistant Examiner* — Karen Thoth
(74) *Attorney, Agent, or Firm* — Gerald E. Hespos; Michael J. Porco; Matthew T. Hespos

(57) ABSTRACT

The present invention relates to a cardiovascular diagnostic system which enables early detection of cardiovascular diseases and defines their causes. Unlike known electrocardiographs, the cardiovascular diagnosis system can further measure elastic coefficient of blood vessels (the degree of arteriosclerosis), blood vessel compliance, blood flow, and blood flow resistance and velocity in blood vessel branches of the right and left coronary arteries. The elastic coefficient shows organic changes to blood vessels. The compliance shows organic and functional changes of blood vessels simultaneously. The blood flow shows blood flow resistance.

72 Claims, 11 Drawing Sheets

CARDIOVASCULAR ANALYZER

CROSS-REFERENCE TO RELATED APPLICATION

This application is a U.S. national stage application of International Application No. PCT/KR2009/005625 filed on Sep. 30, 2009, which claims priority to Korean Patent Application No. 10-2008-0096524 filed on Oct. 1, 2008, the entire contents of which are hereby incorporated by reference.

BACKGROUND OF THE INVENTION

1. Field of the Invention

The present invention relates to a cardiovascular analysis system, and more specifically to a cardiovascular analyzer which enables to detect cardiovascular diseases early and to define their causes. Unlike conventional electrocardiographs, in each branch of the blood vessels of left and right coronary arteries, the cardiovascular analyzer can further measure elastic coefficient of blood vessel (i.e., arterial stiffness) showing organic change, compliance of blood vessel showing organic and functional changes simultaneously, and volume, resistance and velocity of blood flow showing resistance characteristics of blood flow.

2. Description of the Related Art

In the present day, the incidence of vascular and cardiovascular diseases such as arteriosclerosis and myocardial infarction is rapidly increasing due to the meat-oriented dietary lifestyle. But the technology and the instrument for recognizing and preventing the diseases previously are poor.

In today's clinics, the electrocardiograph can't be used to early find out the ischemic diseases and to analyze the function of cardiac blood vessel. Also, the image processing technology and the angiography can be used to diagnose the apparent patient with the diseases because they only show the images of the cardiac blood vessel.

In order to early recognize the symptom of cardiovascular disease such as myocardial infarction, the determination of the coronary artery property, the blood flow characteristics and the blood state is more useful than that of the images of cardiac blood vessel and the electrocardiogram.

The state of blood is easily determined by the blood test. However, the determination of the property of coronary artery and the characteristics of blood flow needs new analyzing instrument.

The most important issue is an exact determination of characteristics of coronary artery. Unlike the other blood vessels, the coronary artery causes vasospasm and vasodilation by the external factors and the epidemiology relationship is complicated with the action of inside pressure of the coronary artery. Consequently, it is very difficult to obtain the properties and characteristics such as arterial stiffness, vascular compliance, blood flow volume, blood flow velocity and blood flow resistance in the coronary artery.

The automatic analyzing electrocardiograph system is widely used in clinics, but it is unable to early find out the risk of incidence of the coronary artery diseases and to determine the patient to surgery by a noninvasive testing method. The electrocardiogram records the electrical changes in the heart but not record the biodynamical properties of cardiac blood vessel such as elastic coefficient of blood vessel, compliance of blood vessel, and volume, resistance and velocity of blood flow.

The coronary artery disease analyzers developed until now are a single photon emission computerized tomography (SPECT), a contrast echocardiography (CE), a multidetector CT (MDCT) and a magnetic resonance imaging (MRI).

On purpose to apply into the surgery of coronary artery, the invasive testing method as catherization has an advantage to directly observe the pathological changes of blood vessel itself but has a need of an essential and complex invasive manipulation of blood vessel. About 40% of examinees have been revealed to person without a need of that surgery.

The electrocardiograph is principally unable to exactly diagnose the ischemic diseases of coronary artery.

Additionally, the mentioned devices have a clinical significance but, owing to high manufacturing and diagnostic cost, are able to be used in the particular hospital only. Commonly, the mentioned devices are unable to detect the properties of blood vessel in spite of little difference.

The property of blood flow in a left coronary artery differs from that of blood flow in a right coronary artery. The blood vessel of left coronary artery is pressed with an additive internal pressure because of the systolic tissue-pressure by the contraction of ventricular myocardium.

Consequently, because the blood flow of the left coronary artery has a very complex structure, the pressure waveform causing the blood flow in the left coronary artery is covered until now.

The right coronary artery perfuses the right ventricle.

The systolic pressure of the right ventricle is about 30% of that of the left ventricle. The pressure of systolic coronary artery is comparably smaller in the right ventricular myocardium.

The invasive testing methods have been widely studied to measure an additive internal pressure transferred from a systolic tissue-internal pressure produced by an intrinsic myocardium contraction in coronary artery. However, until now the noninvasive testing method is insignificantly used to develop the instrument for measuring blood flow volume, blood flow velocity, vascular compliance, elastic coefficient of blood vessel, and blood flow resistance in the coronary artery.

During the last 10 years, the blood flow property of coronary artery has been widely studied and it was found out the blood flow of left coronary artery runs only during the diastole.

At the same time, Japanese researchers discovered that the blood flow also runs during the diastole in the capillary vessel of coronary artery by the radioisotope insertion method.

On the other hand, the property of blood vessel has also been studied. In 2006, Korean and American scientists suggested a method to calculate an elastic coefficient of artery. This method is to calculate an elastic coefficient of blood vessel by measuring atheroma but is difficult to apply to the coronary artery. In addition, in 1997, Ridker and his colleagues of Harvard University have shown that high-sensitivity C-reactive protein has a relationship to cardiovascular diseases. Based on the above study, in 2006, j-CHROMA™ method has been developed to observe the disease process but has not provided information on the state of blood vessel.

However, the present invention provides the measuring methods of blood flow, compliance of blood vessel, blood flow velocity, blood flow resistance, and stiffness of artery (i.e., the degree of arteriosclerosis) in left and right coronary arteries by the synchronous analysis of the electrical property of heart and the biodynamic property of coronary artery.

In order to measure blood flow volume, compliance of blood vessel, blood flow velocity, and blood flow resistance in each branch of left and right coronary arteries, the first issue is to obtain an aortic arch internal pressure curve using the noninvasive testing method.

One related method to obtain the aortic arch internal pressure curve using the noninvasive testing method had been suggested in the international patent publication No. WO1995/016391 (METHOD AND APPARATUS FOR TREATING CARDIOVASCULAR PATHOLOGIES). However, because the curves obtained by the above method are very different from those of the invasive testing method in the same patient, it is virtually impossible to coincide with those curves.

Consequently, it is really impossible that the aortic arch internal pressure curve obtained by the method of WO1995/016391 is extrapolated into clinical trial as like as that curve obtained by using the invasive testing method.

SUMMARY OF THE INVENTION

The present invention is contrived for solving the above-mentioned problems of conventional technology. The objective of the present invention is to provide a cardiovascular analyzer which comprises, unlike the known electrocardiography, to further measure elastic coefficient of blood vessel (i.e., arterial stiffness) showing organic change, compliance of blood vessel showing organic and functional changes simultaneously, and volume, resistance and velocity of blood flow showing resistance characteristics of blood flow in each branch of left and right coronary arteries and enables to detect cardiovascular diseases early and to define their causes.

To achieve the above-mentioned objective, the present invention has the first feature that a cardiovascular analyzer comprises: a bio-signal measurement system including a bio-signal measuring sensor unit which comprises an electrocardiogram (ECG) sensor, a phonocardiogram (PCG) sensor and one or more accelerated plethysmogram (APG) sensors, and a bio-signal reception and process unit which is connected to each of the sensors of the bio-signal measuring sensor unit for receiving and processing bio-signals measured by the sensors; and an analysis indicator calculation system including a main processing unit which is connected to the bio-signal reception and process unit for communicating and calculating biodynamic indicators of a coronary artery from the bio-signals, an input unit which is connected to the main processing unit for receiving control commends of user, and an output unit which is connected to the main processing unit for displaying the calculated results, wherein the main processing unit is configured to synthesize an aortic arch internal pressure curve P from the bio-signals measured by the bio-signal measurement system and to calculate the biodynamic indicators from an area of the aortic arch internal pressure curve P.

The present invention has the second feature that the bio-signal reception and process unit comprises: a microcontroller which controls to process the bio-signals received from the bio-signal measuring unit and to transmit processed bio-signals to the main processing unit; a multi-signal selector which selects one of the bio-signals received from the ECG sensor, the PCG sensor and the APG sensors by a control signal of the microcontroller; a noise eliminator and signal amplifier which eliminates noises and/or controls amplification degree of the bio-signal selected by the multi-signal sensor by a control signal of the microcontroller; a signal switcher which receives the bio-signals from the noise eliminator and signal amplifier and selects one of the bio-signals to meet the control commands of the input unit or of embedded program in the main processing unit by a control signal of the microcontroller; a sample holder which samples and holds the bio-signal selected by the signal switcher by a control signal of the microcontroller; and an A/D converter which converts a holding bio-signal of the sample holder to a digital bio-signal and sends to the microcontroller by a control signal of the microcontroller.

The present invention has the third feature that each of the APG sensors is configured to obtain an APG waveform by sensing a pulse wave due to the pulsatory motion of an artery, and the bio-signal measurement system is configured to obtain an ECG waveform, a PCG waveform and the APG waveform synchronously by the bio-signal measuring sensor unit.

The present invention has the fourth feature that one of the APG sensors is a cuff pulse wave sensor being a cuff sphygmomanometer equipped with a pressure sensor to sense the pulse wave.

The present invention has the fifth feature that the cuff pulse wave sensor comprises a rubber hose which is connected to a air pouch of the cuff sphygmomanometer, a branch hose which is connected to the rubber tube, and an adaptor which is connected to an exit of the branch hose, and the adaptor is connected to the pressure sensor sensing the pulse wave.

The present invention has the sixth feature that the main processing unit is programmed to carry out the steps of: (1) ordering the bio-signal measurement system to measure the bio-signals and receiving the bio-signals from the bio-signal measurement system; (2) analyzing waveforms from the received bio-signals and synthesizing the aortic arch internal pressure curve P from the analyzed waveforms; and (3) calculating the biodynamic indicators from the area of the synthesized aortic arch internal pressure curve P and displaying the results of cardiovascular analysis.

The present invention has the seventh feature that step 3 comprises: calculating blood flow volumes $S_l$ and $S_r$ of the left and right coronary arteries from basic data including the area of the aortic arch internal pressure curve P; calculating compliances $C_l$ and $C_r$ and blood flow resistances $R_l$ and $R_r$ of the left and right coronary arteries from the aortic arch internal pressure curve P and the blood flow volumes $S_l$ and $S_r$ of the left and right coronary arteries; and transmitting the results of cardiovascular analysis to the output unit for showing the calculated compliances $C_l$ and $C_r$ and the calculated blood flow resistances $R_l$ and $R_r$ of the left and right coronary arteries on one C-R chart.

The present invention has the eighth feature that step 3 further comprises: calculating arterial stiffness $As_l$ and $As_r$ of the left and right coronary arteries from the blood flow volumes $S_l$ and $S_r$, the compliances $C_l$ and $C_r$ and the blood flow resistances $R_l$ and $R_r$ of the left and right coronary arteries and transmitting to the output unit.

The present invention has the ninth feature that step 3 further comprises: calculating blood flow velocities $V_l$ and $V_r$ of the left and right coronary arteries from the aortic arch internal pressure curve P and the compliances $C_l$ and $C_r$ of the left and right coronary arteries and transmitting to the output unit.

The present invention has the tenth feature that the blood flow volumes $S_l$ and $S_r$, the compliances $C_l$ and $C_r$ and the blood flow resistances $R_l$ and $R_r$ of the left and right coronary arteries are calculated by the predetermined equations.

The present invention has the eleventh feature that, in the predetermined equations, the coefficient K is calculated by another equation; the coefficient $K_1$ is related to a blood flow volume flowing from an entrance of the coronary artery to the right coronary artery and is 0.12~0.15; and the coefficient $K_2$ is a tissue internal pressure coefficient and is 0.7~0.75.

The present invention has the twelfth feature that the arterial stiffness $As_l$ and $As_r$ of the left and right coronary arteries are calculated by another equations.

The present invention has the thirteenth feature that the blood flow velocities $V_1$ and $V_r$ of the left and right coronary arteries are calculated by another equations.

The present invention has the fourteenth feature that analyzing waveforms from the received bio-signals in step 2 comprises: finding feature points, including systolic upstroke point, systolic peak point, incisura point, diastolic peak point and diastolic end point, of the aortic arch internal pressure curve P by analyzing ECG signals and PCG signals measured by the ECG sensor and the PCG sensor of the bio-signals measurement system, respectively; finding high frequency elements of the aortic arch internal pressure curve P by analyzing Cuff-APG pulse waves measured by a cuff pulse wave sensor, as one of the APG sensors of the bio-signals measurement system, which is pressurized above the systolic blood pressure; finding low frequency elements of the aortic arch internal pressure curve P by analyzing Cuff-APG pulse waves measured by the cuff pulse wave sensor which is depressurized below the diastolic blood pressure; and finding a time-frequency intensity of the aortic arch internal pressure curve P by analyzing APG pulse waves of the left and right carotid arteries measured by a carotid artery pulse wave sensor as one of the APG sensors of the bio-signals measurement system, and wherein the synthesis of the aortic arch internal pressure curve P is based on the basic information including the analyzed data of Cuff-APG pulse waves at the systole and the diastole and the analyzed data of APG pulse waves of the left and right carotid arteries.

The present invention has the fifteenth feature that the main processing unit is further programmed to carry out the steps of: displaying an initial screen including a search menu window, a patient information window, a test and diagnosis window and a test result window in the output unit before step 1; receiving and saving the information of patient if a registration command for new patient is received in the initial screen, otherwise, receiving an opening command to open a registered patient file; displaying a patient list in the registered patient file on the test result window if the opening command is received and receiving a signal for selecting a patient and new information of the selected patient, otherwise, displaying the initial screen continuously; and displaying the information of new patient or the selected patient on the patient information window and receiving a test and diagnosis command, and wherein the information of new patient or the selected patient comprises a personally identified information and body information including one or more of height, weight, blood pressure and race.

The present invention has the sixteenth feature that performance of step 1 by the main processing unit further includes the steps of: (1-1) displaying a command selection window for the bio-signal measurement if a test command is received from the test and diagnosis window, otherwise, keeping the previous state; (1-2-1) receiving ECG, PCG and high frequency APG waveforms measured by the ECG sensor, the PCG sensor and a pressurized cuff pulse wave sensor as one of the APG sensors of the bio-signal measuring sensor unit and displaying on the test result window if the measurement command of a systolic pulse wave is received from the command selection window, otherwise, keeping the previous state as a standby step for receiving a bio-signal measurement command; (1-2-2) receiving ECG, PCG and low frequency APG waveforms measured by the ECG sensor, the PCG sensor and a depressurized cuff pulse wave sensor as one of the APG sensors of the bio-signal measuring sensor unit and displaying on the test result window if the measurement command of a diastolic pulse wave is received from the command selection window, otherwise, keeping the previous state as a standby step for receiving a bio-signal measurement command; (1-2-3) receiving ECG, PCG and left carotid artery APG waveforms measured by the ECG sensor, the PCG sensor and a carotid artery pulse wave sensor as one of the APG sensors of the bio-signal measuring sensor unit and displaying on the test result window if the measurement command of the left carotid artery is received from the command selection window, otherwise, keeping the previous state as a standby step for receiving a bio-signal measurement command; (1-2-4) receiving ECG, PCG and right carotid artery APG waveforms measured by the ECG sensor, the PCG sensor and a carotid artery pulse wave sensor as one of the APG sensors of the bio-signal measuring sensor unit and displaying on the test result window if the measurement command of the right carotid artery is received from the command selection window, otherwise, keeping the previous state as a standby step for receiving a bio-signal measurement command; (1-2-5) receiving ECG, PCG and femoral artery APG waveforms measured by the ECG sensor, the PCG sensor and a femoral artery pulse wave sensor as one of the APG sensors of the bio-signal measuring sensor unit and displaying on the test result window if the measurement command of the femoral artery is received from the command selection window, otherwise, keeping the previous state as a standby step for receiving a bio-signal measurement command; and (1-3) capturing a screen showing a selected ideal waveform among the waveforms displayed on the test result window and saving if a waveform selection command is received after each of steps 1-2-1 to 1-2-5, otherwise, keeping the measurement and displaying the measured waveforms continuously.

The present invention has the seventeenth feature that analyzing waveforms from the received bio-signals and synthesizing the aortic arch internal pressure curve P from the analyzed waveforms in step 2 comprise: (2-1) displaying an analysis menu window if an analysis command is received from the test and diagnosis window, otherwise, keeping the previous step; (2-2) analyzing automatically feature points of the saved ECG, PCG and high frequency APG waveforms and displaying on the test result window if a systolic bio-signal analysis command is received from the analysis menu window, otherwise, keeping the previous step; (2-3) analyzing automatically feature points of the saved ECG, PCG and low frequency APG waveforms and displaying on the test result window if a diastolic bio-signals analysis command is received from the analysis menu window, otherwise, keeping the previous step; (2-4) displaying the saved left and right carotid artery waveforms on the test result window if a synthesized signal analysis command is received from the analysis menu window, otherwise, keeping the previous step; (2-5) displaying enlarged waveforms analyzed in a selected interval on a lower left corner of the test result window if a detail analysis interval is selected in the left and right carotid artery waveforms showing on the test result window, otherwise, keeping the previous step; and (2-6) displaying an aortic arch internal pressure curve, which is synthesized with the information including the saved ECG, PCG and APG waveforms, in a place clicked on the test results window if a vacant space of a lower right corner of the test results window is clicked after the sequential displays of the enlarged left and right carotid artery waveforms on the lower left corner of the test results window, otherwise, keeping the previous step.

The present invention has the eighteenth feature that step 3 comprises: (3-1) displaying a result menu window and a output device icon if a result display command is received from the test and diagnosis window, otherwise, displaying a patient list in the registered patient file on the test result window and receiving a signal for selecting a patient and new information of the selected patient till receiving a command; (3-2) displaying a selected menu result if one is selected on the result menu window, otherwise, keeping step 3-1; and (3-3) outputting the selected menu result if an output command is received from the output device icon after displaying the selected menu result, otherwise, keeping step 3-2.

The present invention has the nineteenth feature that each of steps 2-2, 2-3, and 2-4 causes the main processing unit to return to step 1-1 if a test command is received from the result and diagnosis window after displaying each waveform on the test result window, and wherein if the test command is not received, each of steps 2-2, 2-3, and 2-4 is followed by the subsequent step.

The present invention has the twentieth feature that the result menu window comprises a Compliance-Resistance (C-R) chart; and the C-R chart is divided into sectors to show the coronary artery states according to the clinical results and is dotted to show the states of the left and right coronary arteries of an examinee.

A cardiovascular analyzer of the present invention comprise, unlike the known electrocardiography, to further measure elastic coefficient of blood vessel (i.e., arterial stiffness) showing organic change, compliance of blood vessel showing organic and functional changes simultaneously, and volume, resistance and velocity of blood flow showing resistance characteristics of blood flow in each branch of left and right coronary arteries and enables to early diagnose several refractory diseases such as a myocardial infarction of a coronary artery and to define a patient needed to do surgery of the coronary artery by a non-invasive testing method.

The following reference numbers are used throughout the drawings: reference number 10 indicates a cuff sphygmomanometer, 11 indicates a cuff, 12 indicates an adhesive means (Velcro), 13 indicates an air pouch, 14, 17 and 18 indicate a rubber hose, 15 indicates an air valve, 16 indicates an air supply means, 20 indicates an adapter, 21 indicates a branch hose, 22 indicates an attachment part of branch hose, 24 indicates a cover, 26 indicates a projecting part for connecting to adapter, 30 indicates a pressure sensor, 31 indicates a vent hole, 32 indicates an opening part, 34 indicates a housing body, 36 indicates a sensing read line, 40 indicates an aortic arch, 42 indicates a left coronary artery, 44 indicates a right coronary artery, 50 indicates an aortic arch internal pressure curve obtained by a catheter, 60 indicates an aortic arch internal pressure curve obtained by the present invention, 70 indicates a test result window of output unit, 71 and 72 indicate an ECG waveform, 73 and 74 indicate a PCG waveform, 75 indicates a high frequency APG waveform, 76 indicates a low frequency APG waveform, 77 indicates a left carotid artery APG waveform, 78 indicates a right carotid artery APG waveform, 81 indicates an amplified left carotid artery APG waveform, 82 indicates an amplified right carotid artery APG waveform, and 83 indicates a synthesized aortic arch internal pressure curve.

DETAILED DESCRIPTION OF THE PREFERRED EMBODIMENTS

A detailed description of preferred embodiments of the present invention is provided below with respect to accompanying drawings. Because the present invention can be embodied in various forms, the technical idea of the present invention has to be not limited to the drawings and the embodiments described herein.

Figure 1:
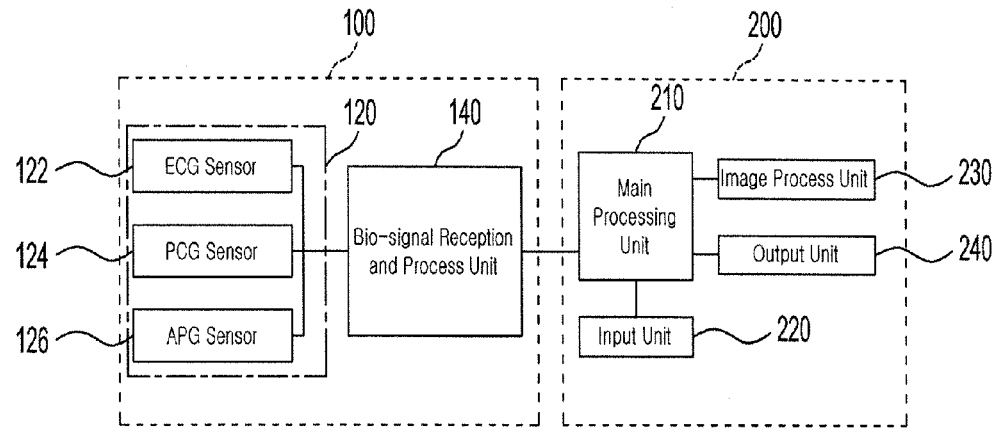
FIG. 1 is a block diagram of a cardiovascular analyzer according to an exemplary embodiment of the present invention.
Figure 2:
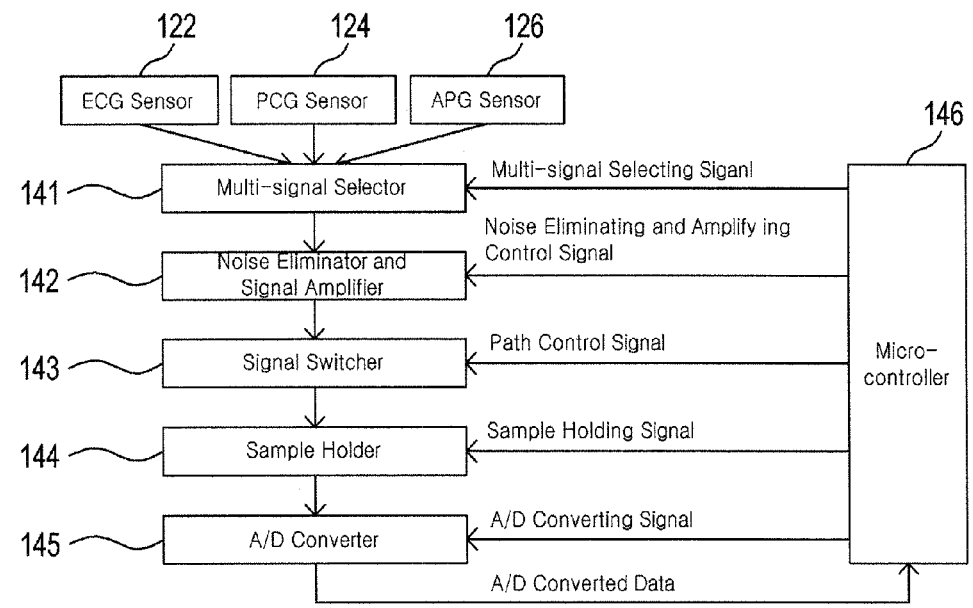
FIG. 2 is a block diagram conceptually showing the constitution and the signal flow of the bio-signal reception and process unit in FIG. 1.
Figure 3:
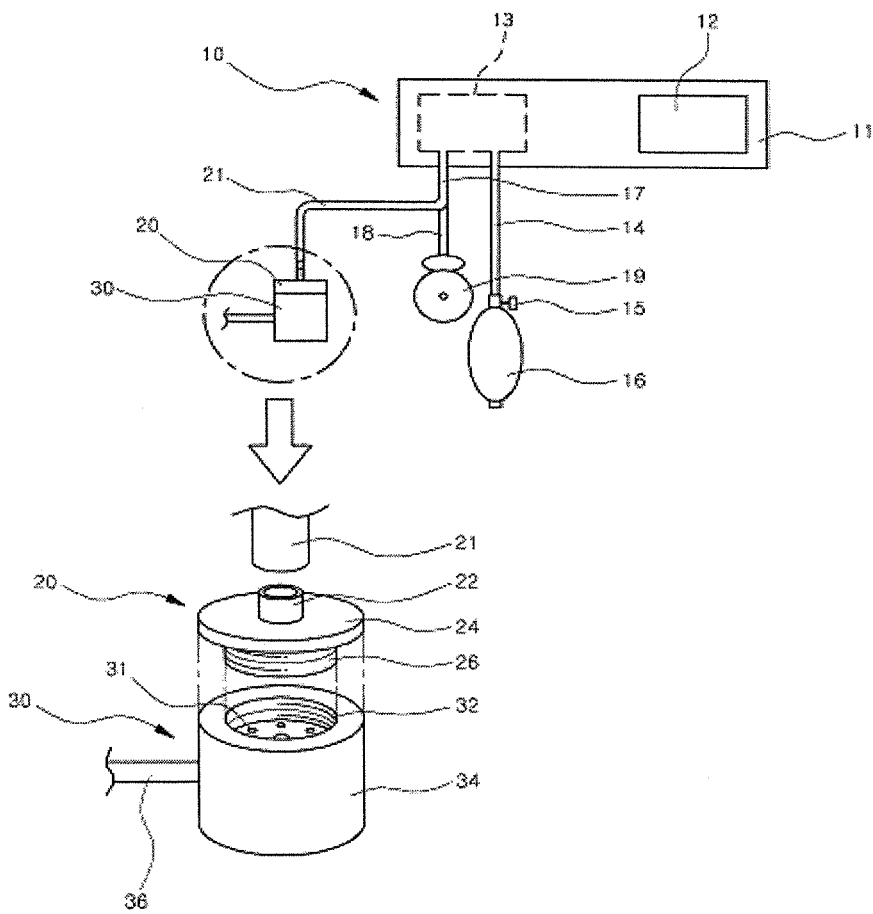
FIG. 3 is a front and disassembled perspective views of a cuff pulse wave sensor as the APG sensor showed in FIG. 1.
Figure 4:
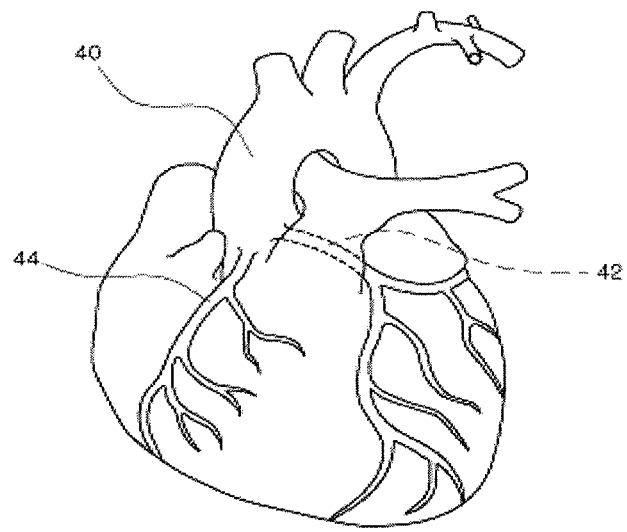
FIG. 4 is a representative diagram of cardiac blood flow showing an aortic arch and left and right coronary arteries connected to the aortic arch.
Figure 5:
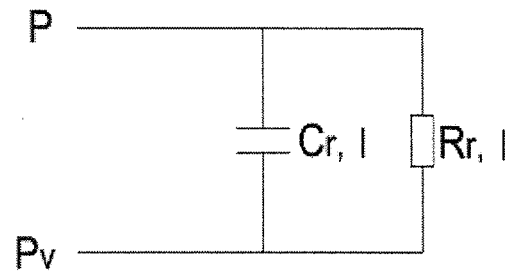
FIG. 5 is a model diagram of elasticity of the left and right coronary arteries according to the present invention.
Figure 6:
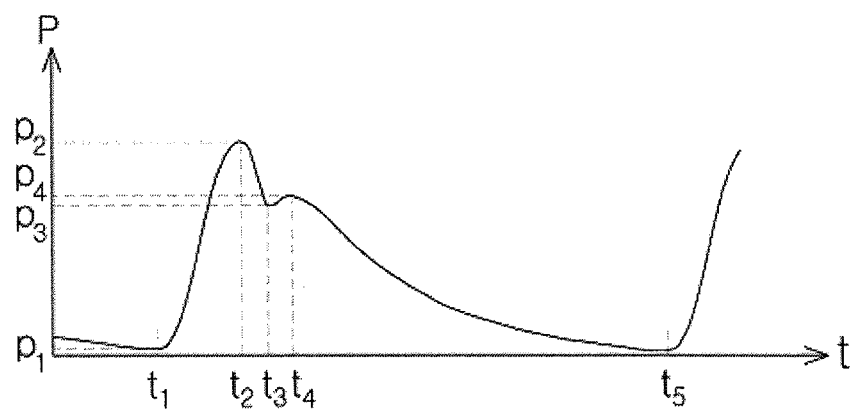
FIG. 6 is a blood pressure property diagram showing feature points and pressures of an aortic arch internal pressure curve obtained by a catheter.
Figure 7:
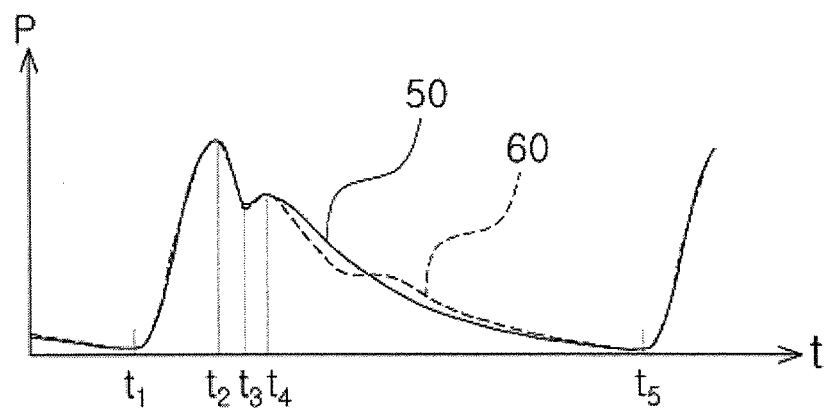
FIG. 7 is a comparative diagram of the aortic arch internal pressure curves obtained by a catheter or by the present invention.

FIG. 1 is a block diagram of a cardiovascular analyzer according to an exemplary embodiment of the present invention. FIG. 2 is a block diagram conceptually showing the constitution and the signal flow of the bio-signal reception and process unit in FIG. 1. FIG. 3 is a front and disassembled perspective views of a cuff pulse wave sensor as the APG sensor showed in FIG. 1. FIG. 4 is a representative diagram of cardiac blood flow showing an aortic arch and left and right coronary arteries connected to the aortic arch. FIG. 5 is a model diagram of elasticity of the left and right coronary arteries according to the present invention. FIG. 6 is a blood pressure property diagram showing feature points and pressures of an aortic arch internal pressure curve obtained by a catheter. And FIG. 7 is a comparative diagram of the aortic arch internal pressure curves obtained by a catheter or by the present invention.

As shown in FIG. 1, a cardiovascular analyzer according to one embodiment of the present invention is characterized by basically comprising: a bio-signal measurement system 100 including a bio-signal measuring sensor unit 120 which comprises an electrocardiogram (ECG) sensor 122, a phonocardiogram (PCG) sensor 124 and an accelerated plethysmogram (APG) sensor 126, and a bio-signal reception and process unit 140 which is connected to the bio-signal measuring sensor unit 120 for receiving and processing bio-signals measured by each sensor of the bio-signals measuring sensor unit 120; and an analysis indicator calculation system 200 including a main processing unit 210 which is connected to the bio-signal reception and process unit 140 for communicating and calculating biodynamic indicators of a coronary artery from the bio-signals, an input unit 220 which is connected to the main processing unit 210 for receiving control commends of user, and an output unit 230 which is connected to the main processing unit 210 for displaying the calculated results, wherein the main processing unit 210 synthesizes an aortic arch internal pressure curve P from the bio-signals measured by the bio-signal measurement system 100 and calculates the biodynamic indicators from an area of the aortic arch internal pressure curve P.

Here, the ECG sensor 122 comprises at least three electrodes and is used to obtain an ECG waveform and to define the feature points (i.e., systolic upstroke point, systolic peak point, incisura point, diastolic peak point and diastolic end point) of the aortic arch internal pressure curve P with the PCG sensor.

The PCG sensor 124 comprises a microphone to perceive the sound of open-and-shut of heart valves and is used to obtain a PCG waveform for defining the feature points of the aortic arch internal pressure curve P.

The APG sensor 126 is used to obtain an APG waveform by sensing a pulse wave of the pulsatory motion. The APG sensor 126 comprises a pressure sensor having a piezoelectric element, but not limited to, or other device which senses the pulse wave.

In this embodiment, the APG sensor 126 is one of the sensors including a cuff pulse wave sensor to get information for a frequency spectrum of an aortic arch, a carotid artery pulse wave sensor to get information for a probability density spectrum of the aortic arch by directly measuring pulse waves of the left and right carotid arteries, and a femoral artery pulse sensor to get information for a pulse wave velocity (PWV) etc by directly measuring a pulse wave of the femoral artery.

Here, it is possible that the carotid artery pulse wave sensor and the femoral artery pulse wave sensor are the same kind of pressure sensor. The cuff pulse wave sensor is a cuff sphygmomanometer equipped with a pressure sensor.

As an embodiment, the detailed structure of the cuff pulse wave sensor is shown in FIG. 3. A branch hose 21 is connected to a rubber hose 14 or 17 which is connected to an air pouch 13 in the cuff sphygmomanometer 10. An adaptor 20 is connected to an exit of the branch hose 21 and is assembled to an opening part 32 of a sensor (e.g. a pressure sensor 34) having the same structure as the carotid artery pulse wave sensor or the femoral artery pulse wave sensor.

As above mentioned, the bio-signal measuring sensor unit 110 essentially comprises the ECG sensor 122, the PCG sensor 124 and the APG sensor 126 for sensing the different bio-signals. The device embedded with the bio-signal reception and process unit 140 has at least three connectors for connecting to each of the sensors of the bio-signal measuring sensor unit 110.

Also, as shown in FIG. 2, the bio-signals reception and process unit 140 comprises: a microcontroller 146 which controls to process the bio-signals received from the bio-signal measuring unit 120 and to transmit processed bio-signals to the main processing unit 210; a multi-signal selector 141 which selects one of the bio-signals received from the ECG sensor 122, the PCG sensor 124 and the APG sensor 126 by a control signal of the microcontroller 146; a noise eliminator and signal amplifier 142 which eliminates noises and/or controls amplification degree of the bio-signal selected by the multi-signal sensor 141 by a control signal of the microcontroller 146; a signal switcher 143 which receives the bio-signals from the noise eliminator and signal amplifier 142 and selects one of the bio-signals to meet the control commands of the input unit 220 or of embedded program in the main processing unit 210 by a control signal of the microcontroller 146; a sample holder 144 which samples and holds the bio-signal selected by the signal switcher 143 by a control signal of the microcontroller 146; and an A/D converter 145 which converts a holding bio-signal of the sample holder 144 to a digital bio-signal and sends to the microcontroller 146 by a control signal of the microcontroller 146.

Here, the multi-signal selector 141 is used to sequentially process the signals which are simultaneously measured and inputted by the ECG sensor 122, the PCG sensor 124 and the APG sensor 126. The noise eliminator and signal amplifier 142 is used to make a standard waveform by filtering the noises of the obtained bio-signals and to control an amplification degree according to a patient (examinee).

As above mentioned, the bio-signal reception and process unit 140 is preferable to involve in the bio-signal measurement system 100 but, according to a circuit design, can be embedded in the main processing unit 210.

Next, the bio-signals obtained and processed by the bio-signal measurement system 100 is transferred to the analysis indicator calculator system 200 for synthesizing the aortic arch internal pressure curve P. The area of the aortic arch internal pressure curve P is used to calculate the biodynamic indicators.

As shown in FIG. 1, when the bio-signal reception and process unit 140 is separated from the main processing unit 210, a predetermined communicating means (e.g., RS-232C) is used to exchange the data between them.

The main processing unit 210 is a core unit, as like as a central processing unit (CPU) of computer, to process the measured data from the bio-signal reception and process unit 140 by the program saved in an internal memory part or an external memory part for calculating the biodynamic indicators which is used to analyze the coronary artery.

Here, the biodynamic indicators for analysis of the coronary artery are blood flow volumes $S_l$ and $S_r$, compliances $C_l$ and $C_r$, blood flow resistances $R_l$ and $R_r$, arterial stiffness $As_l$ and $As_r$, and blood flow velocities $V_l$ and $V_r$ of the left and right coronary arteries.

First, the definition and the relationship of the biodynamic indicators used in this embodiment are simply described.

The blood flow volume is the volume of blood flowing in the left or right coronary artery. The unit of blood flow volume is ml, Q or Q(t) is used to express as a function of time, and S is used to express a blood volume having flowed for a time period (i.e., integral of Q for time). The blood flow volume is generally in direct proportion to the difference P-Pv of blood pressures and in inverse proportion to the blood flow resistance R between two sites longitudinally separated in the coronary artery. The small value of the blood flow volume causes the ischemic symptoms.

The compliance is a change of volume occurred at the unit volume of blood vessel forced by the unit force. The unit of compliance is ml/mmHg and the compliance is simply written as C. The small value of C means the more stiffness or contraction of the blood vessel wall. On the contrary, the large value of C means the more flex or extending spasm occurs in the blood vessel wall.

The blood flow resistance means the resistance against the flow of blood in the left or right coronary artery. The unit of blood flow resistance is mmHg/l, and is simply written as R. R is approximately determined by the rate of the difference P-Pv of the blood pressures and the blood flow volume Q between two sites longitudinally separated in the coronary artery.

The arterial stiffness Asc is an indicator showed how much power is needed to change the unit length of blood vessel and, in other words, showed the stiffness of blood vessel. The Asc reflects the organic change of blood vessel. The unit of Asc is $Kg/cm^2$ and Asc is generally proportional to the square of the propagation velocity of elastic wave.

Lastly, the blood flow velocity V is the speed of blood flowing in the left or right coronary artery and the unit of V is cm/s. The pulse wave velocity (PWV) reflects the elastic status of an aorta and is measured by method recording pulse wave in the carotid artery and the femoral artery. The more stiffness of blood vessel wall is the more rapid of the velocity. Especially, the harder change of arteriosclerosis is the more rapid of the velocity of blood flow or the pulse wave velocity.

Also, in the words of the described biodynamic indicators, a subscript 'l' means a 'left' and a subscript 'r' means a 'right'.

On the other hand, the main processing unit 210 is connected to the input unit 220 for receiving the control commands of user and to the output unit 240 for displaying the results calculated in the main processing unit 210.

Here, the output unit 240 comprises a screen output part through a monitor as well as a printer. Therefore, the image process unit 230 of FIG. 1 can be embedded in the screen output part.

Also, the input unit 220 comprises not only a keyboard and a mouse, but also a touch input means on the monitor of the screen output part.

In the above mentioned configuration, the core part is the calculation of the biodynamic indictors by some equations using the measurement and analysis of the bio-signals under the control of the main processing unit 210. Therefore, it is described in detail.

Figure 8:
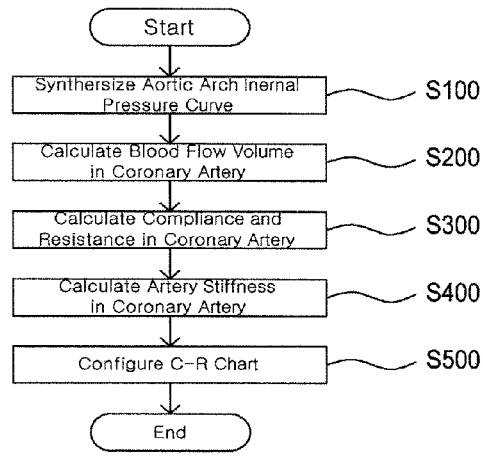
FIG. 8 is an exemplary flowchart of the main processing unit showed in FIG. 1.

As shown in FIG. 8, the control of the main processing unit 210 comprises the steps of: step S100, synthesizing the aortic artery internal pressure curve P from the bio-signals measured by the bio-signal measurement system 100; step S200, calculating the blood flow volumes of the left and right coronary arteries using the synthesized aortic artery internal pressure curve P; step S300, calculating the C and R of the left and right coronary arteries based on the aortic artery internal pressure curve P and the blood flow volumes of the left and right coronary arteries; step S400, calculating the stiffness of the left and right coronary arteries based on the calculated biodynamic indicators; and step S500, displaying a status diagram (e.g., C-R chart) in the output unit 240 by transmitting the calculated biodynamic indicators.

By the way, the control of the main processing unit 210 can be carried out by a program embedded in the main processing unit 210. The control program of the main processing unit 210 basically comprises the steps of: (1) ordering the bio-signal measurement system 100 to measure the bio-signals and receiving the bio-signals from the bio-signal measurement system 100; (2) analyzing waveforms from the received bio-signals and synthesizing the aortic arch internal pressure curve P from the analyzed waveforms; and (3) calculating the biodynamic indicators from the area of the synthesized aortic arch internal pressure curve P and displaying the results of cardiovascular analysis. The control of the main processing unit 210 can be variously carried out by the program as follows.

Above all, in the step 1 to measure the bio-signals by the bio-signal measurement system 100, it is preferable to control as the following protocols: the ECG, PCG and Cuff-APG signals are simultaneously measured by the ECG sensor 122, the PCG sensor 124 and a cuff pulse wave sensor, as the APG sensor 126, which is pressurized to 10~15 mmHg more than the systolic blood pressure; the ECG, PCG and Cuff-APG signals are simultaneously measured by the ECG sensor 122, the PCG sensor 124 and the cuff pulse wave sensor 126 which is depressurized to 20~30 mmHg less than the diastolic blood pressure; the ECG, PCG and left carotid artery APG signals are simultaneously measured by the ECG sensor 122, the PCG sensor 124 and a left carotid artery pulse wave sensor as the APG sensor 126; the ECG, PCG and right carotid artery APG signals are simultaneously measured by the ECG sensor 122, the PCG sensor 124 and a right carotid artery pulse wave sensor as the APG sensor 126; and the ECG and femoral artery APG signals are simultaneously measured by the ECG sensor 122 and a femoral artery pulse wave sensor as the APG sensor 126.

Also, in step 2 the waveform analysis of the received bio-signals comprises, first of all, analyzing the ECG and PCG signals measured by the ECG sensor 122 and the PCG sensor 124 of the bio-signals measurement system 100, respectively, for finding the feature points of the aortic arch internal pressure curve P.

Here, the feature points of the aortic arch internal pressure curve P, as shown in FIG. 6, are systolic upstroke point t1, systolic peak point t2, incisura point t3, diastolic peak point t4 and diastolic end point t5.

Next, the high frequency elements of the aortic arch internal pressure curve P is found by the analysis of Cuff-APG pulse wave (i.e., systolic Cuff-APG pulse wave) measured by a cuff pulse wave sensor, as the APG sensor of the bio-signals measurement system 100, which is pressurized above the systolic blood pressure.

Next, the low frequency elements of the aortic arch internal pressure curve P is found by the analysis of Cuff-APG pulse wave (i.e., diastolic Cuff-APG pulse wave) measured by a cuff pulse wave sensor, as the APG sensor of the bio-signals measurement system 100, which is depressurized below the diastolic blood pressure.

As like as mentioned below, it is based on the facts that the frequency spectrum of the aortic arch internal pressure curve P is identical to the Cuff-APG pulse wave which is measured by the cuff pulse wave sensor 126 under the pressurized or depressurized states with a predetermined pressure.

Next, the time-frequency intensity of the aortic arch internal pressure curve P is found by the analysis of APG pulse waves of the left and right carotid arteries measured by a carotid artery pulse wave sensor as the APG sensor 126 of the bio-signal measurement system 100.

As like as mentioned below, it is based on the facts that the spectrum of probability density of the aortic arch internal pressure curve P is identical to the APG pulse wave of the left or right carotid artery measured by the carotid artery pulse wave sensor 124.

And, in the step 2, the synthesis of the aortic arch internal pressure curve P is based on the information including the analyzed data of Cuff-APG pulse waves at the systole and the diastole and the analyzed data of APG pulse waves of the left and right carotid arteries.

Also, in the step 3, calculating the biodynamic indicators from the area of the aortic arch internal pressure curve P for showing the cardiovascular analysis results is based on the facts that, as like as mentioned below, the synthesized aortic arch internal pressure curve P 60 has a different waveform, but has the same area as the aortic arch internal pressure curve P 50 which is measured by the invasive testing method using a catheter as shown in FIG. 7.

The step 3 for calculating the biodynamic indicators comprises specifically: calculating blood flow volumes $S_l$ and $S_r$ of the left and right coronary arteries from the basic data including the area of the synthesized aortic arch internal pressure curve P; calculating compliances $C_l$ and $C_r$ and blood flow resistances $R_l$ and $R_r$ of the left and right coronary arteries from the aortic arch internal pressure curve P and the blood flow volumes $S_l$ and $S_r$ of the left and right coronary arteries; and transmitting the results of cardiovascular analysis to the output unit for showing the calculated compliances $C_l$ and $C_r$ and the calculated blood flow resistances $R_l$ and $R_r$ of the left and right coronary arteries on one status diagram (e.g., C-R chart).

At this time, the blood flow volumes $S_l$ and $S_r$, the compliances $C_l$ and $C_r$ and the blood flow resistances $R_l$ and $R_r$ of the left and right coronary arteries are calculated by the following equations.

The blood flow volume $S_l$ of the left coronary artery is $$S_l = KA_d \left( \frac{t_* + \Delta t_d}{\Delta t_d} \right) \qquad \text{Equation 1}$$

The blood flow volume $S_r$ of the right coronary artery is $$S_r = K_1 pR^2 (1-\upsilon^2)^{1/2} Pm(1+Ad/K_2As)/(\rho a) \qquad \text{Equation 2}$$

The compliance $C_l$ of the left coronary artery is $$C_l = \frac{\left( S_l - \frac{A_d}{R_l} \right)}{(P_* - P_d)} \qquad \text{Equation 3}$$

The compliance $C_r$ of the right coronary artery is $$C_r = \frac{k_2 A_S - A_d}{P_S^* - P_d} \cdot \frac{S_r}{k_2 A_S + A_{d_i}} \qquad \text{Equation 4}$$

The blood flow resistances $R_{l1}$ and $R_{l2}$ of the left coronary artery are $$R_{l_1} = \frac{P_d - P_v}{S_l} \qquad \text{Equation 5}$$

$$R_{l_2} = \frac{\bar{P}}{S_v} \qquad \text{Equation 6}$$

And the blood flow resistance $R_r$ of right coronary artery is $$Rr = \frac{k_2 A_S + A_d}{Sr} \qquad \text{Equation 7}$$

In Equations 1 to 7, Ad is an area of the aortic arch internal pressure curve P at diastole, As is an area of the aortic arch internal pressure curve P at systole, t* is a time to a point which the first-order derivative function of the aortic arch internal pressure curve P is zero at systole, υ is Poisson constant of blood vessel, R is an equivalent radius of blood vessel, Pm is an average blood pressure, ρ is a blood density, a is a propagation velocity of pulse wave, Pd is a blood pressure of the aortic arch internal pressure curve P at diastole, Ps is a blood pressure of the aortic arch internal pressure curve P at systole, P* and Ps* are blood pressure of the aortic arch internal pressure curve P at an incisura point, $P_v$ is a blood pressure of the left coronary artery at random point, $S_v$ is a cardiac output, and K, $K_1$ and $K_2$ are coefficients.

Here, the coefficient K is calculated by Equation 8. The coefficient $K_1$ is related to a blood flow volume flowing from an entrance of the coronary artery to the right coronary artery and is 0.12~0.15. The coefficient $K_2$ is a tissue internal pressure coefficient and is 0.7~0.75.

$$K = kA \cdot \sqrt{C_s} \qquad \text{Equation 8}$$
$$= kA \left[ (2mP_d + 1) \cdot \frac{\frac{A_d}{R} - n(P_*^2 - P_d^2)}{(P_* - P_d) + m(P_*^2 - P_d^2)} + 2nP_d \right]$$

In Equation 8, k is a coefficient related to a blood flow volume flowing from an entrance of the coronary artery to the left coronary artery and is 0.85~0.88, $A=\pi R^2$ is an equivalent area of the left coronary artery, $C_s$ is a compliance at systole, and m and n are Cope constants.

Also, it is preferable that the step 3 further comprises calculating arterial stiffness $As_l$ and $As_r$ of the left and right coronary arteries from the blood flow volumes $S_l$ and $S_r$, the compliances $C_l$ and $C_r$ and the blood flow resistances $R_l$ and $R_r$ of the left and right coronary arteries and transmitting to the output unit 240.

At this time, the arterial stiffness $As_l$ and $As_r$ of the left and right coronary arteries are calculated by the following Equations 9 and 10.

The arterial stiffness $As_l$ of the left coronary artery is $$As_l = K_3 \frac{R_{l_1}^{0.25}}{C_l R_{l_1}} (1 - S_l) \qquad \text{Equation 9}$$

And the arterial stiffness $As_r$ of the right coronary artery is $$Asr = K_3 \frac{Rr^{0.25}}{CrRr} (1 - S_r) \qquad \text{Equation 10}$$

In Equations 9 and 10, $K_3$ is a coefficient derived from the clinics and is 0.7~0.89.

In addition, it is preferable that the step 3 further comprises calculating blood flow velocities $V_l$ and $V_r$ of the left and right coronary arteries from the aortic arch internal pressure curve P and the compliances $C_l$ and $C_r$ of the left and right coronary arteries and transmitting to the output unit 240.

At this time, the blood flow velocities $V_l$ and $V_r$ of the left and right coronary arteries are calculated by the following Equations 11 and 12.

The blood flow velocity $V_l$ of the left coronary artery is $$V_l = \frac{C_l}{A_0} \left( \frac{dp}{dt} \right)_{DW} \qquad \text{Equation 11}$$

And the blood flow velocity $V_r$ of the right coronary artery is $$Vr = \frac{C_r}{A_0} \left( \frac{dp}{dt} \right)_{DW} \qquad \text{Equation 12}$$

In Equations 11 and 12, $$\left(\frac{dp}{dt}\right)_{DW} = \frac{P(x_1, t_2) - P(x_1, t_1)}{t_2 - t_1}$$

Next, referring to FIGS. 9 to 16, the more specific control embodiments of the main processing unit 210 are described.

Figure 13:
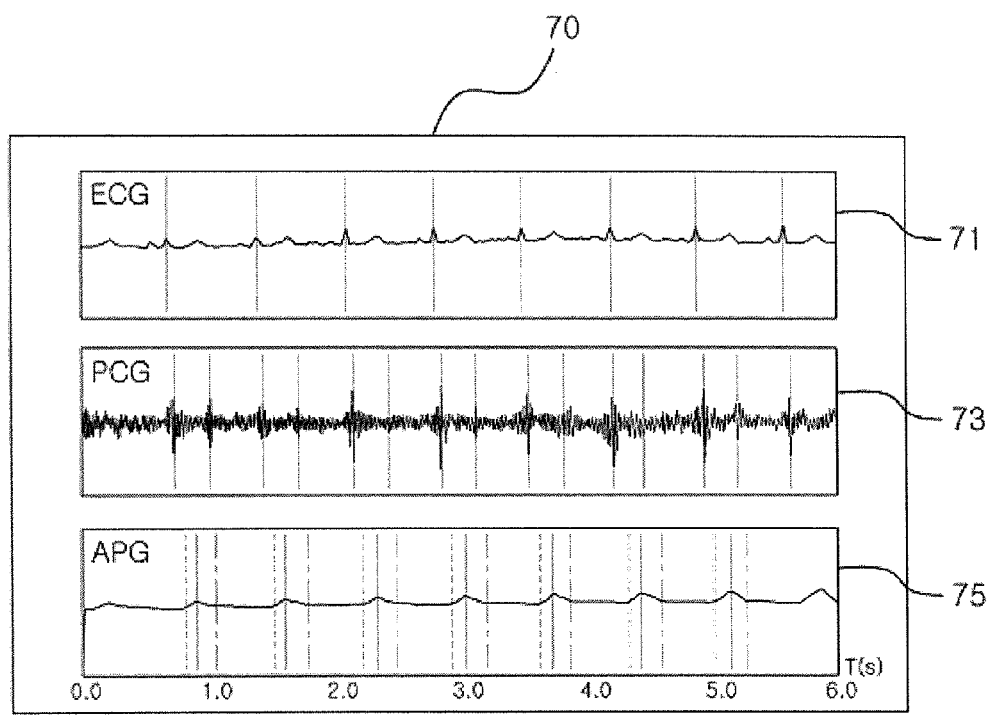
FIG. 13 is an exemplary diagram of the test and result window showing ECG, PCG and high frequency APG waveforms analyzed by the main processing unit in FIG. 1.
Figure 14:
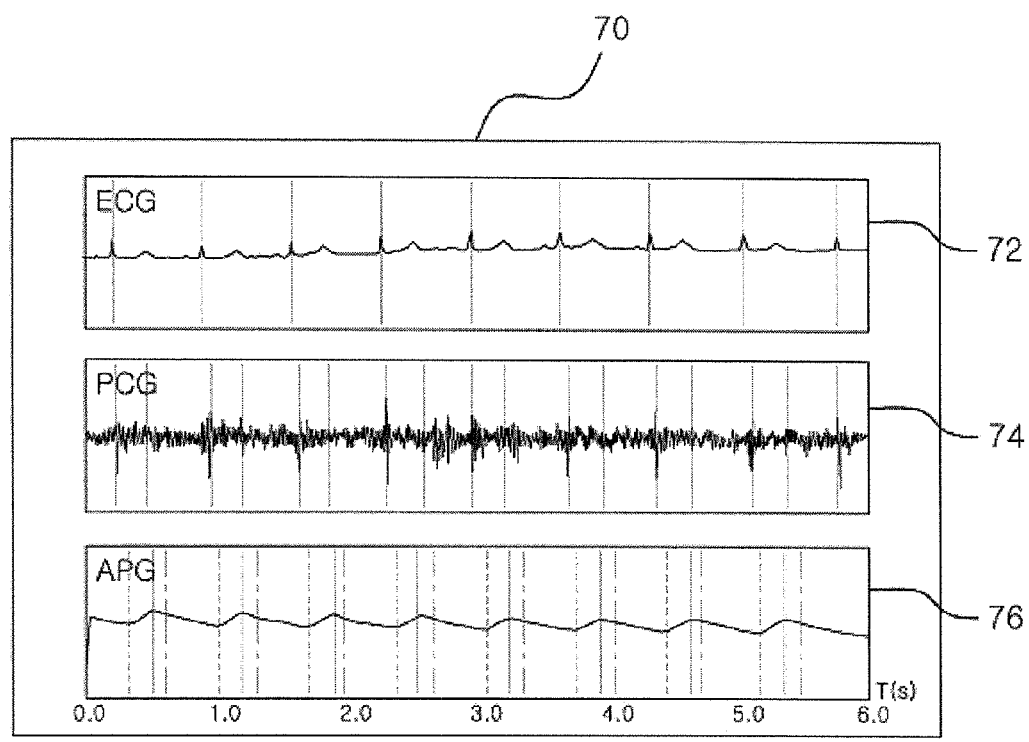
FIG. 14 is an exemplary diagram of the test and result window showing ECG, PCG and low frequency APG waveforms analyzed by the main processing unit in FIG. 1.
Figure 15:
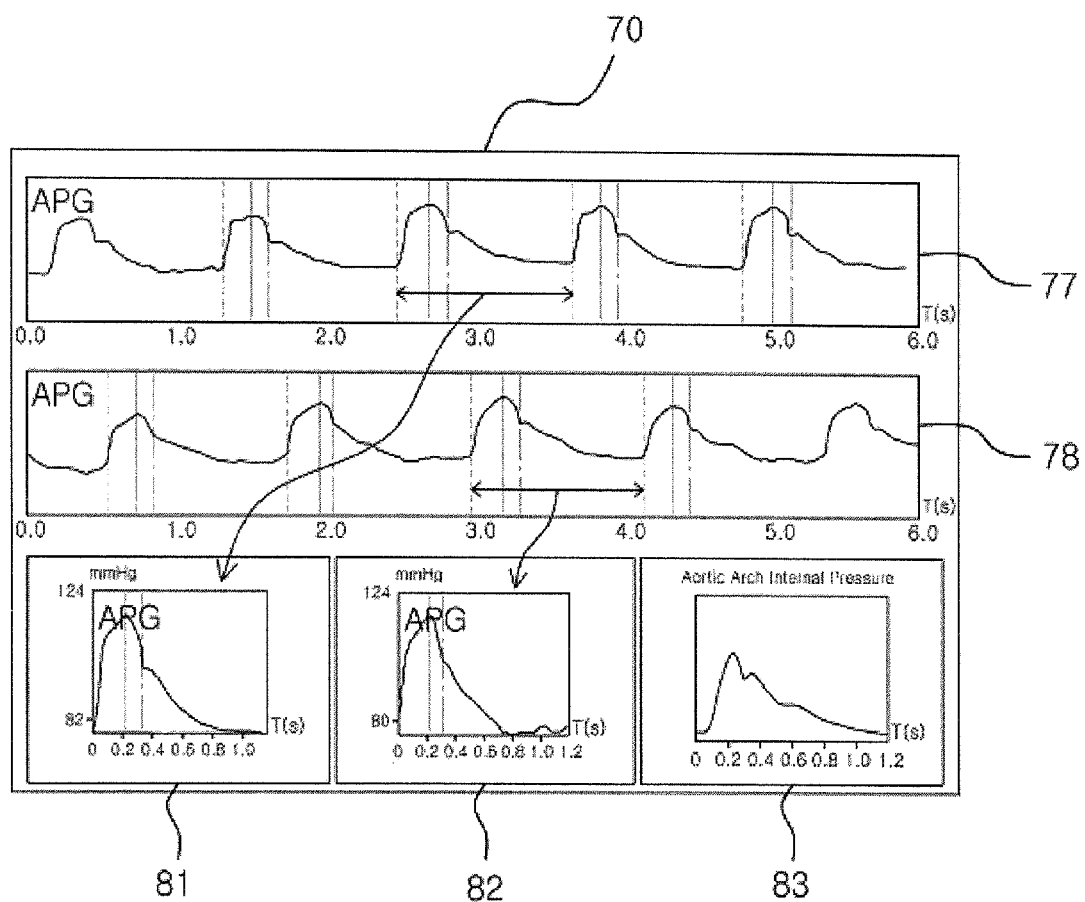
FIG. 15 is an exemplary diagram of the test and result window showing left and right carotid artery APG waveforms analyzed by the main processing unit in FIG. 1.
Figure 16:
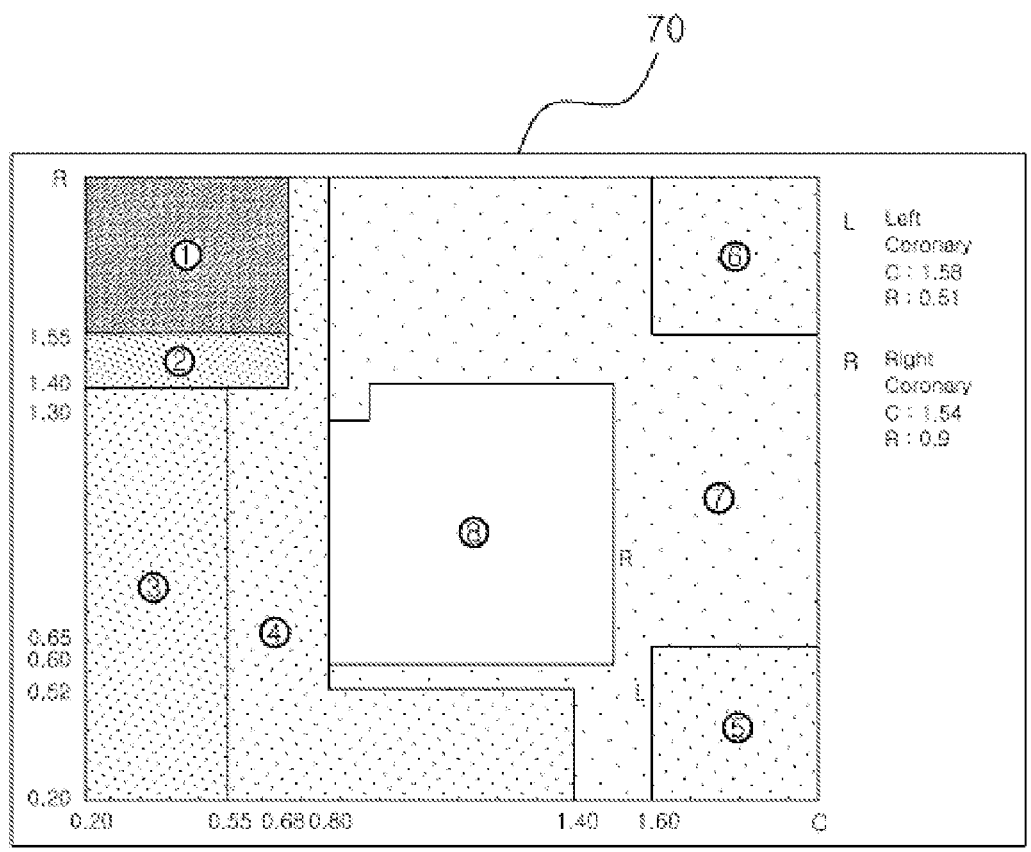
FIG. 16 is an exemplary diagram of the test and result window showing C-R chart analyzed by the main processing unit in FIG. 1.

FIGS. 9 to 12 are exemplary flowcharts showing more detail than FIG. 8. FIG. 13 is an exemplary diagram of the test and result window showing ECG, PCG and high frequency APG waveforms analyzed by the main processing unit in FIG. 1. FIG. 14 is an exemplary diagram of the test and result window showing ECG, PCG and low frequency APG waveforms analyzed by the main processing unit in FIG. 1. FIG. 15 is an exemplary diagram of the test and result window showing left and right carotid artery APG waveforms analyzed by the main processing unit in FIG. 1. FIG. 16 is an exemplary diagram of the test and result window showing C-R chart analyzed by the main processing unit in FIG. 1.

Figure 9:
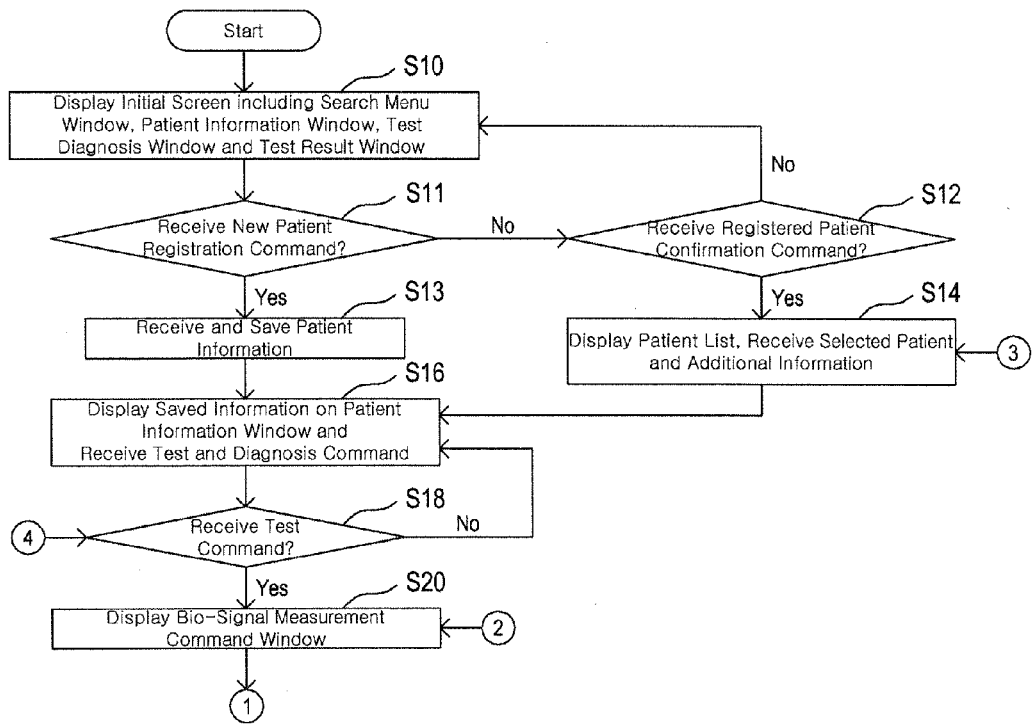
FIGS. 9 to 12 are exemplary flowcharts showing more detail than FIG. 8.

As shown in FIG. 9, the main processing unit 210 is further programmed to display an initial screen including a search menu window, a patient information window, a test and diagnosis window and a test result window in the output unit 240 before the step 1 (S10).

And the main processing unit 210 makes to receive and save the information of patient if a registration command for new patient is received in the initial screen (S13), otherwise, to receive an opening command to open a registered patient file (S12).

Next, the main processing unit 210 makes to display a patient list in the registered patient file on the test result window if the opening command is received and to receive a signal for selecting a patient and new information of the selected patient (S14), otherwise, to display the initial screen continuously.

Next, the main processing unit 210 makes to display the information of new patient or the selected patient on the patient information window and to receive a test and diagnosis command (S18).

Here, the information of new patient or the selected patient preferably comprises a personally identified information and body information including one or more of height, weight, blood pressure and race. Especially, the height, blood pressure, race and etc can be used to calculate the biodynamic indicators as the basic data of the patient (examinee).

Figure 10:
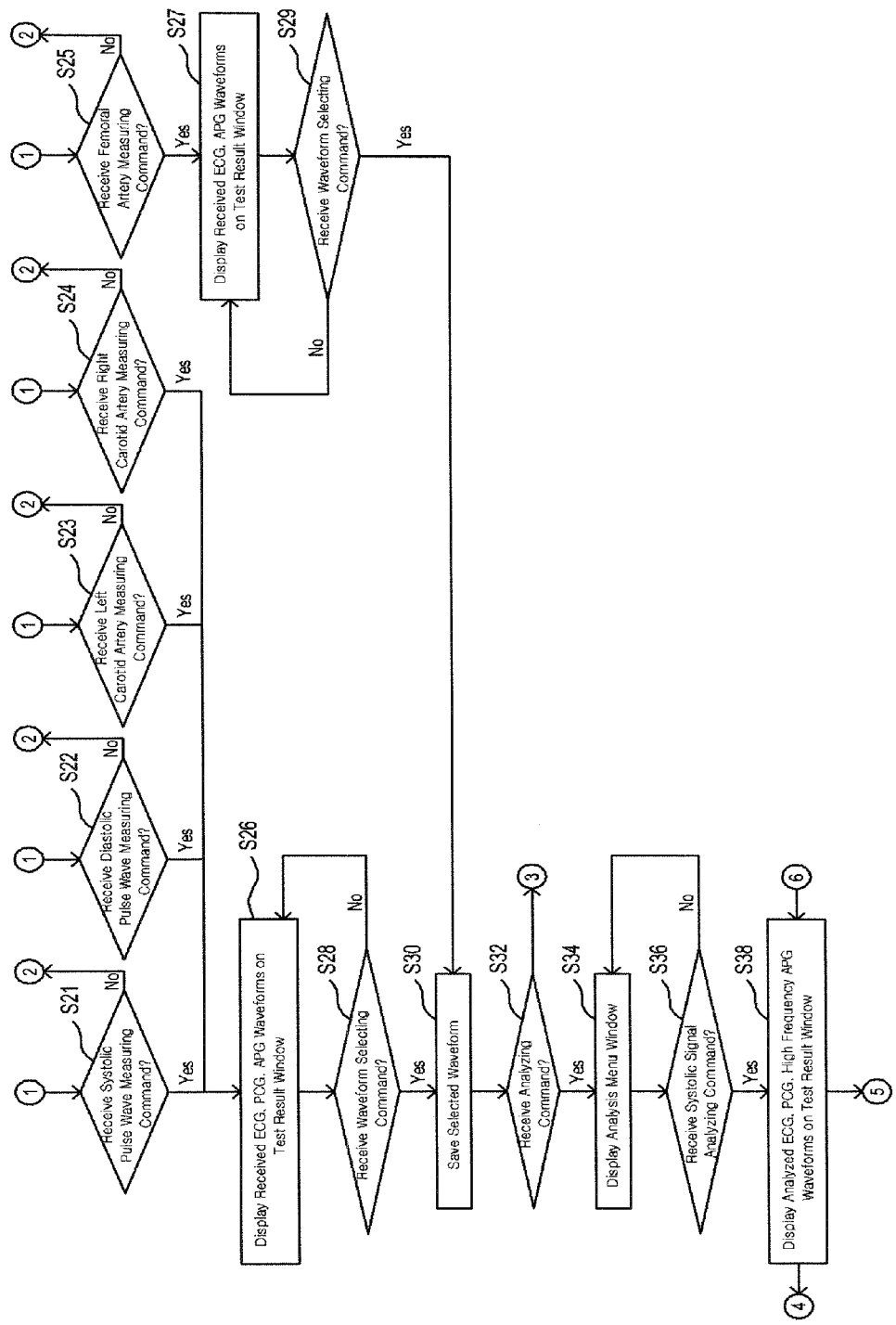

Afterward, the measurement and reception of the bio-signals in the step 1, as shown in FIGS. 9 and 10, comprises the following steps.

First of all, as a step 1-1, the main processing unit 210 makes to display a command selection window for the bio-signal measurement 100 (S20) if a test command is received from the test and diagnosis window (S18), otherwise, to keep the previous state.

Next, as a step 1-2-1, the main processing unit 210 makes to receive ECG, PCG and high frequency APG waveforms measured by the ECG sensor 122, the PCG sensor 124 and a pressurized cuff pulse wave sensor as the APG sensor 126 of the bio-signal measuring sensor unit and to display on the test result window (S26) if the measurement command of a systolic pulse wave is received from the command selection window (S21), otherwise, to keep the previous state as a standby step for receiving a bio-signal measurement command.

As a step 1-2-2, the main processing unit 210 makes to receive ECG, PCG and low frequency APG waveforms measured by the ECG sensor 122, the PCG sensor 124 and a depressurized cuff pulse wave sensor as the APG sensor 126 of the bio-signal measuring sensor unit and to display on the test result window (S26) if the measurement command of a diastolic pulse wave is received from the command selection window (S22), otherwise, to keep the previous state as a standby step for receiving a bio-signal measurement command.

As a step 1-2-3, the main processing unit 210 makes to receive ECG, PCG and left carotid artery APG waveforms measured by the ECG sensor 122, the PCG sensor 124 and a carotid artery pulse wave sensor as the APG sensor 126 of the bio-signal measuring sensor unit and to display on the test result window (S26) if the measurement command of the left carotid artery is received from the command selection window (S23), otherwise, to keep the previous state as a standby step for receiving a bio-signal measurement command.

As a step 1-2-4, the main processing unit 210 makes to receive ECG, PCG and right carotid artery APG waveforms measured by the ECG sensor 122, the PCG sensor 124 and a carotid artery pulse wave sensor as the APG sensor 126 of the bio-signal measuring sensor unit and to display on the test result window (S26) if the measurement command of the right carotid artery is received from the command selection window (S24), otherwise, to keep the previous state as a standby step for receiving a bio-signal measurement command.

As a step 1-2-5, the main processing unit 210 makes to receive ECG, PCG and femoral artery APG waveforms measured by the ECG sensor 122, the PCG sensor 124 and a femoral artery pulse wave sensor as the APG sensor 126 of the bio-signal measuring sensor unit and to display on the test result window (S27) if the measurement command of the femoral artery is received from the command selection window (S25), otherwise, to keep the previous state as a standby step for receiving a bio-signal measurement command.

And, as a step 1-3, the main processing unit 210 makes to capture a screen showing a selected ideal waveform among the waveforms displayed on the test result window and to save (S30) if a waveform selection command is received after each of the steps 1-2-1 to 1-2-5 (S28, S29), otherwise, to keep the measurement and to display the measured waveforms continuously.

Here, when the ideal waveforms do not display on the test result window, the received signals are controlled by the noise eliminator and signal amplifier 142 through the input unit 220 and the microcontroller 146.

Figure 11:
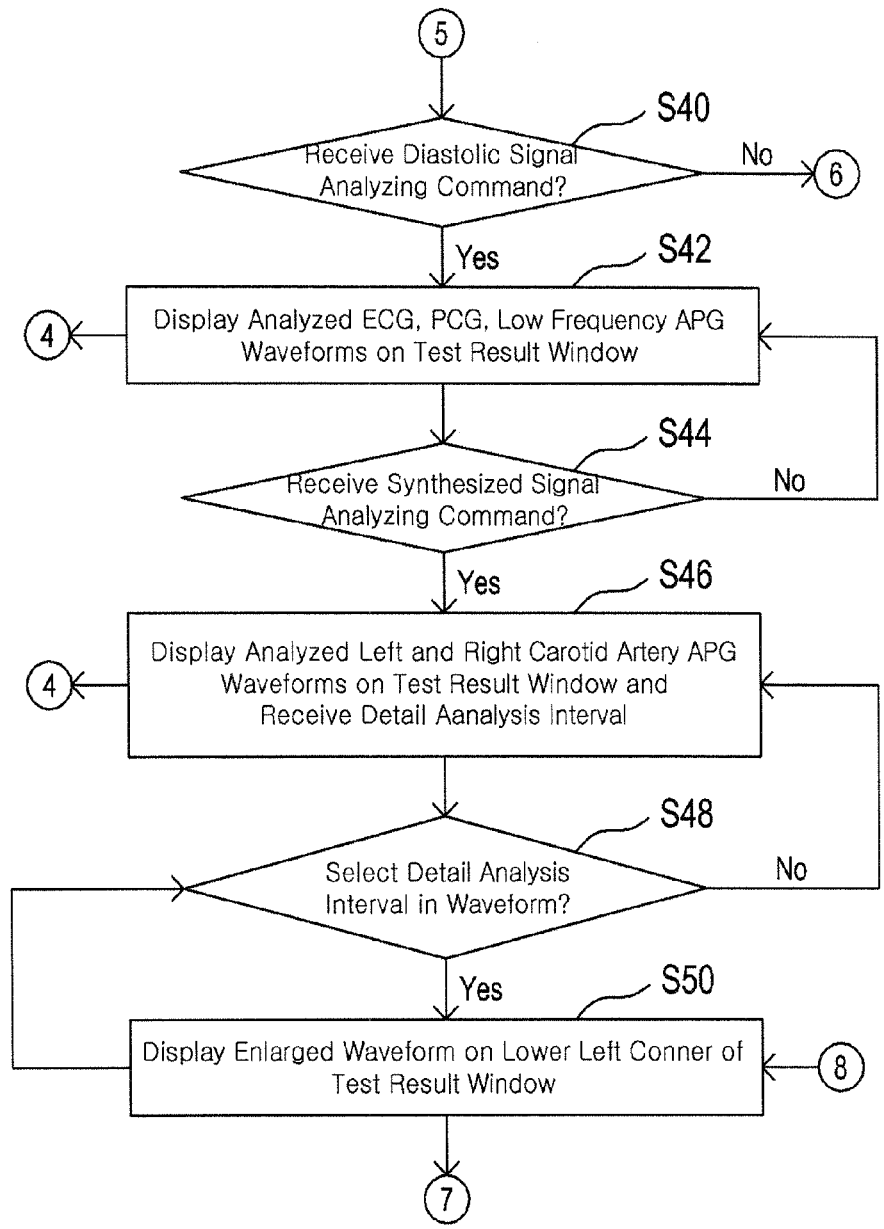
Figure 12:
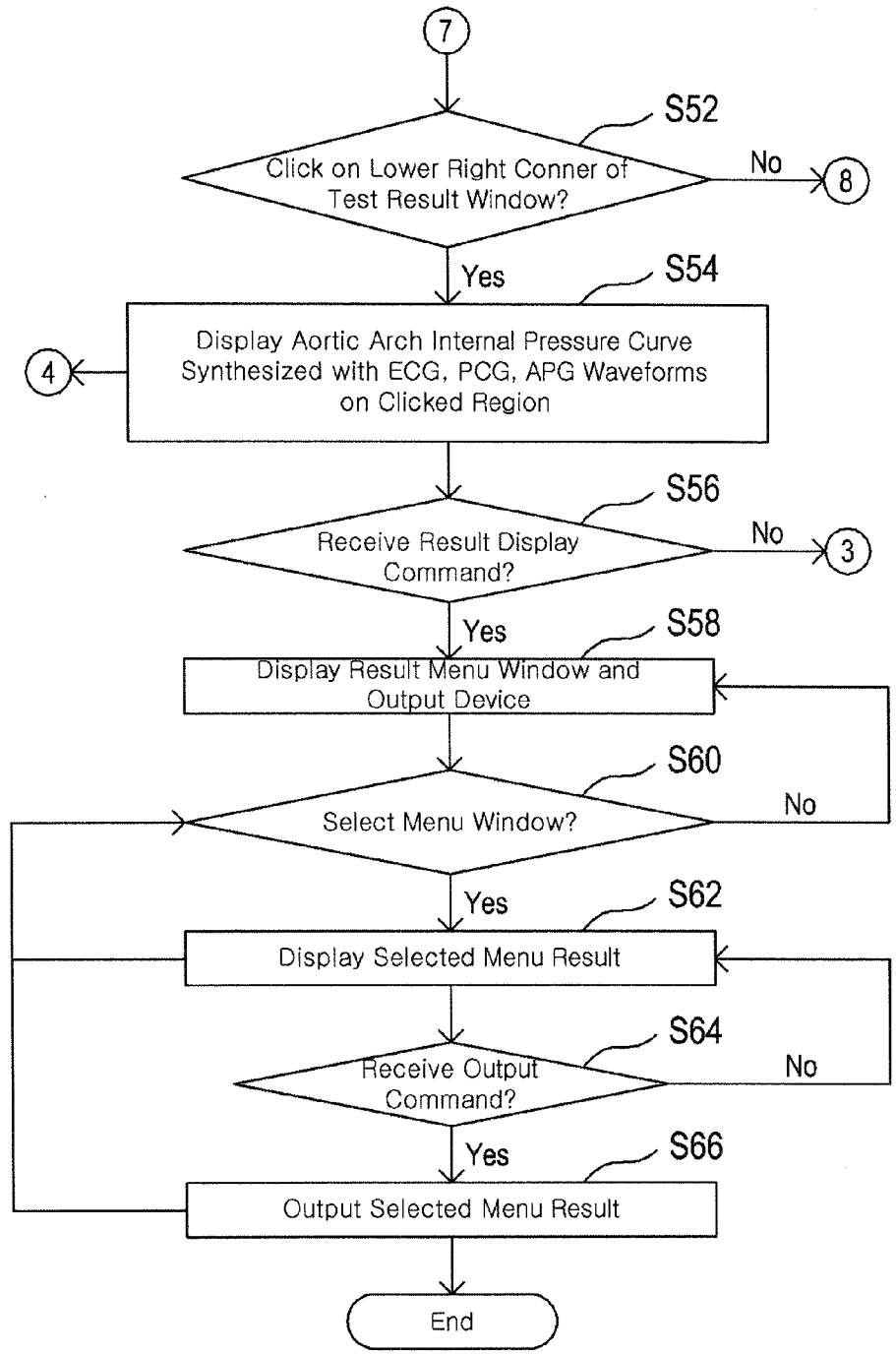

Also, the waveform analysis of the received bio-signals and the synthesis of the aortic arch internal pressure curve P in the step 2, as shown in FIGS. 10 to 12, comprise the following steps.

As a step 2-1, the main processing unit 210 makes to display an analysis menu window (S34) if an analysis command is received from the test and diagnosis window (S32), otherwise, to keep the previous step.

As a step 2-2, the main processing unit 210 makes to analyze automatically feature points of the saved ECG waveform 71, PCG waveform 73 and high frequency APG waveform 75 and to display on the test result window 70 as shown in FIG. 13 (S38) if a systolic bio-signal analysis command is received from the analysis menu window (S36), otherwise, to keep the previous step.

As a step 2-3, the main processing unit 210 makes to analyze automatically feature points of the saved ECG waveform 72, PCG waveform 74 and low frequency APG waveform 76 and to display on the test result window 70 as shown in FIG. 14 (S42) if a diastolic bio-signals analysis command is received from the analysis menu window (S40), otherwise, to keep the previous step.

As a step 2-4, the main processing unit 210 makes to display the saved left and right carotid artery waveforms 77 and 78 on the test result window 70 as shown in FIG. 15 (S46) if a synthesized signal analysis command is received from the analysis menu window (S44), otherwise, to keep the previous step.

As a step 2-5, the main processing unit 210 makes to display enlarged waveforms 81 and 82 analyzed in a selected interval on a lower left corner of the test result window 70 as shown in FIG. 15 (S50) if a detail analysis interval is selected in the left and right carotid artery waveforms 77 and 78 showing on the test result window 70 (e.g., by the mouse dragging in FIG. 15) (S48), otherwise, to keep the previous step.

As a step 2-6, the main processing unit 210 makes to display an aortic arch internal pressure curve 83, which is synthesized with the information including the saved ECG, PCG and APG waveforms, in a place clicked on the test results window 70 (S54) if a vacant space of a lower right corner of the test results window 70 is clicked after the sequential displays of the enlarged left and right carotid artery waveforms 81 and 82 on the lower left corner of the test results window 70 (S52), otherwise, to keep the previous step.

At this time, it is preferable that the main processing unit 210 makes to return to the step 1-1 after displaying each waveform on the test result window in the steps 2-2 to 2-4 (S38, S42, S46) if a test command is received from the result and diagnosis window (S18), otherwise, to go to each next step.

Finally, the step 3 showing the results of cardiovascular analysis through the calculation of the biodynamic indicators from the area of the synthesized aortic arch internal pressure curve P, as shown in FIG. 12, comprises the following steps.

As a step 3-1, the main processing unit 210 makes to display a result menu window and a output device (S58) if a result display command is received from the test and diagnosis window (S56), otherwise, to keep the previous step.

As a step 3-2, the main processing unit 210 makes to display a selected menu result (S62) if one is selected on the result menu window (S60), otherwise, to keep the previous step.

As a step 3-2, the main processing unit 210 makes to output the selected menu result (S66) if an output command is received from the output device after displaying the selected menu result (S64), otherwise, to keep the previous step.

At this time, the result menu window, as shown in FIG. 16, preferably comprises a C-R chart assessment. The C-R chart divides into sectors to show the coronary artery states according to the clinical results. The result of the C-R chart assessment is dotted on the C-R chart to show the states of the left and right coronary arteries of an examinee.

It is reasonable that the sectors of C-R chart, as shown in FIG. 16, can be divided to increase the precision according to the various results of clinics. By the exemplary embodiment of clinical result, the sectors can be defined as the followings.

Sector ① is the cardiovascular stenosis area. Although a symptom does not show, a coronary artery stenosis should be suspected. If examinees have the symptom, 90% or more of them have a coronary artery obstructed with 50% or more.

Sector ② is the very suspicious area of cardiovascular stenosis. If examinees have the symptom, 80% or more of them can be diagnosed as stenosis.

Sector ③ is the suspicious area of cardiovascular stenosis. If examinees have the symptom, they can be examined and treated pursuant to the obstruction.

Sector ④ is the area with about 50% frequency of the cardiovascular stenosis. If examinees have the symptom, the cardiovascular state can be determined as bad even though it comes with a normal cardiovascular angiography.

Sector ⑤ is the area of cardiovascular extending spasm. Although a symptom does not show, the state can be diagnosed as an abnormal and the observation is needed. This can be suspected the drug over-dose for abnormal extension of coronary artery.

Sector ⑥ is the suspected area of the instability of cardiovascular blood flow because of the micro-regurgitation in blood vessel by internal pressure of myocardial tissue or others. Frequently, it is normal in the cardiovascular angiography. The observation is needed according to the symptom.

Sector ⑦ is the area generally diagnosed as a normal. The states of bloodstream and blood vessel are not normal, but are shown with no obstruction in the cardiovascular angiography.

Sector ⑧ is the normal area.

In the followings, the supplementary theories and clinical data are described to support the above mentioned embodiments.

The blood flows in the left coronary artery only at diastole. The research result is proved by the observation of the movement of the light marked niobium element in the coronary artery using the CCD type in vivo microscopy.

In the present invention, it is considered blood to flow in the left coronary artery only at diastole by the tissue internal pressure and the self control property of myocardium occurred at systole of heart.

From the fact, it is suggested that the systole and diastole of aortic arch 40 is as like as a heart to supply blood to the left and right coronary arteries 42 and 44 in the view of the blood circulation of coronary artery (ref FIG. 4).

On the other hand, the systolic pressure of right ventricle is 25-30% of that of left ventricle and the systole of myocardium in the right ventricle wall presses weakly the coronary artery. So, in the right coronary artery the maximum bloodstream is occurred at systole of heart and the waveform of the bloodstream has a pressure property in proportion to the aortic arch internal pressure curve.

On the other hand, according to other experimental data, blood flow volume changes linearly with blood pressure at the systole and diastole of blood vessel under 170 of blood pressure. So, the compliance of systolic blood vessel is the same as that of diastolic blood vessel.

Therefore, the problem of finding an area of the aortic arch internal pressure curve by the noninvasive testing method is the same as the problem of solving the pump function of heart tank for assessing the blood circulation of coronary artery, in other words, the working of pump to supply the blood to coronary artery.

Thus, first at the problem of configuration of the aortic arch internal pressure curve, the most accurate waveform and systolic and diastolic blood pressures in the aortic arch can be measured by the invasive testing method as plug the catheter in the blood vessel and then draw the aortic arch internal pressure curve.

However, because it is not really usable in such a way, the aortic arch internal pressure curve has to be obtained by the noninvasive testing method. The frequency spectrum (i.e., the strength analysis in frequency space) of the aortic arch internal pressure curve is consisted of high and low frequencies.

To solve this problem, first look at the problem to obtain the most obvious waveforms of the high and low frequency spectra by the noninvasive testing method.

If blood pressure is measured at the state pressurized above the systolic blood pressure or depressurized below the diastolic blood pressure after wearing on the cuff of examinee with a cuff pulse wave sensor as shown in FIG. 3, the waves formed by the vibration of blood flow is transmitted from the air pouch 13 of cuff pulse wave sensor. And the vibration waveforms of cuff pulse wave can be obtained by a computer.

The waveform displayed on the computer is formed by the air in the air pouch of cuff pulse wave sensor, but not the pulse wave itself. However, the waves measured by the cuff pulse wave sensor in the arm (i.e., cuff) accurately transmit the whole process of blood flow to the computer. The pressurized or depressurized pressure given to the cuff pulse wave sensor is caused the high or low frequency curve, respectively.

Thus, it can be obtained a spectrum which is similar to the spectrum of the aortic arch internal pressure curve if Cuff-APG pulse wave is measured under a predetermined pressure.

But, the problem is that how the blood pressure points can be defined as the maximum systolic point $P_s$ and the minimum diastolic point $P_d$ for drawing the Cuff-APG pulse wave curves similar to the high and low frequency spectra of the aortic arch internal pressure curve obtained by the invasive testing method, respectively.

First, when it is written that $P_{sis}$ is the systolic pressure measured by sphygmomanometer, $P_{dia}$ is the diastolic pressure measured by sphygmomanometer, $P_{sis}^*$ is the systolic pressure to cause the high frequency spectrum, and $P_{dia}^*$ is the diastolic pressure to cause the low frequency spectrum, the related equations are as followings.

$$P^*sis = Psis + \Delta 1 \quad \text{Equation 13}$$

$$P^*dia = Pdia - \Delta 2 \quad \text{Equation 14}$$

On the other hand, Tables 1 and 2 are showing the conduit test data measured from 24 examinees by the catheter and the cuff pulse wave sensor.

TABLE 1

Comparison of Systolic Blood Pressures measured by Catheter and Cuff pulse wave sensor

| Blood Pressure Type | Frequency | Cuff Sensor | Conduit System | Blood Pressure Difference | $\Delta_1$ Percent (%) | Remarks |
|---|---|---|---|---|---|---|
| Low blood pressure | 3 | 100 | 110 | 10 | 10 | |
| Normal | 4 | 120 | 130 | 10 | 9.2 | |
| blood pressure | 3 | 140 | 151 | 11 | 7.8 | |
| High | 4 | 160 | 172 | 12 | 7.5 | |
| blood | 5 | 180 | 192 | 12 | 6.7 | |
| pressure | 5 | 200 | 212 | 12 | 6 | |
| Total | 24 | | | 11.16 | 7.8 | |

TABLE 2

Comparison of Diastolic Blood Pressures measured by Catheter and Cuff pulse wave sensor

| Blood Pressure Type | Frequency | Cuff Sensor | Conduit System | Blood Pressure Difference | $\Delta_2$ Percent (%) | Remarks |
|---|---|---|---|---|---|---|
| Low blood pressure | 3 | 70 | 50 | 20 | 28 | |
| Normal | 4 | 80 | 57 | 23 | 28.7 | |
| blood pressure | 3 | 90 | 62 | 27 | 30 | |
| High | 4 | 100 | 70 | 30 | 30 | |
| blood | 5 | 110 | 76 | 34 | 31 | |
| pressure | 5 | 120 | 84 | 38 | 31.6 | |
| Total | 24 | | | 20~38 | 29.5 | |

As obtained from Table 1, if the pulse wave is measured considering about 11 and 20~38 for the systolic and diastolic blood pressure, respectively, the systole point and the diastole point can be found to draw the waveform with a frequency spectrum similar to that of the aortic arch internal pressure curve.

But, it can't be used to construct the real pulse wave because the wave measured by the cuff pulse wave sensor is a perturbation wave which is transmitted to the air in the air pouch of cuff pulse wave sensor. However, by properly matching the measured wave, the waveform with frequency similar to that of the blood pressure waveform obtained by Doppler can be drawn.

However, because the probability density spectrum (i.e., the strength analysis in frequency space) of the aortic arch internal pressure curve is obviously different from that of the perturbation wave, these two waves are different from each other. Especially, the form and height of incisura point are very different.

On the other hand, because a carotid artery pulse wave is a wave which is not formed by the vibration in the air pouch of Cuff-APG but measured on a surface wave of blood vessel. And it has not a reflecting point. So the probability density spectrum of the carotid artery pulse wave is similar to that of the aortic arch internal pressure curve.

However, the frequency spectrum of the carotid artery pulse wave is very different from that of the aortic arch internal pressure curve.

Therefore, in the present invention, the aortic arch internal pressure curve is synthesized with the carotid artery pulse wave, the perturbation wave at the maximum systolic point, and the perturbation wave at the minimum diastolic point. At this time, the blood pressures are the same at the feature points of the waves measured by the invasive and noninvasive testing methods.

In other words, the blood pressure of the systolic cuff pulse wave is $$P_{cs} = \frac{\alpha Pss}{\alpha + \beta + \gamma} + \frac{\beta Pds}{\alpha + \beta + \gamma} + \frac{\gamma P_c}{\alpha + \beta + \gamma} \quad \text{Equation 15}$$

And the blood pressure of the diastolic cuff pulse wave is $$P_{cd} = P_{dia} + \frac{\beta}{\gamma + \beta}[P_{dia} - P_{ds}(t)] + \frac{\gamma}{\gamma + \beta}[P_{dia} - P_c(t)] \quad \text{Equation 16}$$

In the incisura point, it must be satisfied with the following condition.

$$\left[\frac{\alpha Pss(t_s)}{\alpha + \beta} + \frac{\beta Pds(t_s)}{\alpha + \beta} \frac{\gamma P_c(t_s)}{\alpha + \beta + \gamma}\right] = \quad \text{Equation 17}$$

$$P_{dia} + \frac{\beta}{\gamma + \beta}[P_{dia} - P_{ds}(t_s)] + \frac{\gamma}{\gamma + \beta}[P_{dia} - P_c(t_s)]$$

where Pss is a blood pressure at the systolic point, Pds is a blood pressure at the diastolic point, Pc is a blood pressure in the carotid artery, and Ps is a blood pressure at the incisura point.

In Equations 15 to 17, a, β, and γ are calculated by solving the minimum values of a functional J[u(a, β, γ)] which is the difference between the pulse waveform of the intravascular ultrasound Doppler and the synthesized curve.

As above mentioned, it is impossible to synchronize the invasive and noninvasive aortic arch internal pressure curves because a, β, and γ are very different and very large in the range of fluctuation in each examinee.

However, the area of the invasive aortic arch internal pressure curve is not different from that of the noninvasive aortic arch internal pressure curve between persons.

Therefore, in the present invention, the methods are suggested to obtain the clinical indicators using the area data of the invasive and noninvasive aortic arch internal pressure curves.

In this perspective, Equations 14 to 17 are transformed as followings.

In other words, the area of the blood pressure of the systolic cuff pulse wave is $$\int_0^{ts} P_{cs} dt = \int_0^{ts} \left[ \frac{\alpha(Pss+\Delta_1)}{\alpha+\beta+\gamma} + \frac{\beta(Pds+\Delta_1)}{\alpha+\beta+\gamma} + \frac{\gamma(P_c+\Delta_1)}{\alpha+\beta+\gamma} \right] dt \quad \text{Equation 18}$$

And the area of the blood pressure of the diastolic cuff pulse wave is $$\int_{ts}^{td} P_{cd} dt = \int_{ts}^{td} \left[ P_{dia} - \Delta_2 + \frac{\beta}{\gamma+\beta}[P_{dia} - P_{ds}(t)] + \frac{\gamma}{\gamma+\beta}[P_{dia} - P_c(t)] \right] dt \quad \text{Equation 19}$$

In the incisura point, it must be satisfied with the following condition.

$$\left[ \frac{\alpha Pss(t_s)}{\alpha+\beta} + \frac{\beta Pds(t_s)}{\alpha+\beta} \frac{\gamma P_c(t_s)}{\alpha+\beta+\gamma} \right] = \quad \text{Equation 20}$$

$$P_{dia} + \frac{\beta}{\gamma+\beta}[P_{dia} - P_{ds}(t_s)] + \frac{\gamma}{\gamma+\beta}[P_{dia} - P_c(t_s)]$$

Next, a, β, and γ are calculated by solving the minimum values of a functional J[u(a, β, γ)] which is the difference between the pulse waveform of the intravascular ultrasound Doppler and the synthesized curve.

By solving the minimum values of the functional J(u) using the conduit test data measured from 24 examinees, a, β, and γ are obtained as followings.

TABLE 3

| Conduit Test Data of 24 Examinees | | | |
|---|---|---|---|
| No | α | β | γ |
| 1 | 0.22 | 0.13 | 0.65 |
| 2 | 0.21 | 0.14 | 0.66 |
| 3 | 0.20 | 0.13 | 0.64 |
| 4 | 0.20 | 0.13 | 0.63 |
| 5 | 0.24 | 0.12 | 0.64 |
| 6 | 0.24 | 0.14 | 0.65 |
| 7 | 0.21 | 0.13 | 0.66 |
| 8 | 0.22 | 0.14 | 0.64 |

TABLE 3-continued

| Conduit Test Data of 24 Examinees | | | |
|---|---|---|---|
| No | α | β | γ |
| 9 | 0.23 | 0.14 | 0.63 |
| 10 | 0.23 | 0.13 | 0.64 |
| 11 | 0.24 | 0.14 | 0.62 |
| 12 | 0.20 | 0.15 | 0.65 |
| 13 | 0.22 | 0.14 | 0.64 |
| 14 | 0.23 | 0.14 | 0.63 |
| 15 | 0.23 | 0.15 | 0.62 |
| 16 | 0.26 | 0.13 | 0.61 |
| 17 | 0.22 | 0.13 | 0.62 |
| 18 | 0.23 | 0.12 | 0.63 |
| 19 | 0.24 | 0.12 | 0.64 |
| 20 | 0.23 | 0.14 | 0.63 |
| 21 | 0.24 | 0.14 | 0.62 |
| 22 | 0.25 | 0.13 | 0.61 |
| 23 | 0.23 | 0.12 | 0.64 |
| 24 | 0.21 | 0.12 | 0.63 |

From the data of Table 3, the area of the aortic arch internal pressure curve can be calculated where a=0.22, β=0.13, and γ=0.65.

Next, it is regarding to obtain the clinical indicators for assessing the state of blood vessel of coronary artery.

As above mentioned, in the left coronary artery, the blood starts to flow at diastole, but not at systole.

Because the change of coronary artery is very small and almost isotropic deformation, the compliance of systole is approximately same to that of diastole. So the compliance of the left coronary artery can be considering as that of the coronary artery even though it is calculated by the diastolic blood pressure causing blood flow in the left coronary artery and the deformation of the left coronary artery.

By this idea and from the model diagram of FIG. 5, when Ts=t<T, the pulse waveform P(t) is obtained as Equation 21.

$$C_l \frac{dP}{dt} + \frac{P - P_v}{R_l} = Q_l \quad \text{Equation 21}$$

In Equation 21, $R_l$ is the peripheral resistance of the left coronary artery, $C_l$ is the compliance of the left coronary artery, and $Q_l$ is the blood flow volume in the left coronary artery.

According to the experimental data, the relationship between pressure and volume in blood vessel shows that the deformation of blood vessel is linearly proportional to the pressure by around 170 mmHg of blood pressure.

Thus, $C_l$ is a constant as like as followings.

$$C_l = \frac{\left(S_l - \frac{A_d}{R_l}\right)}{(P_* - P_d)} \quad \text{Equation 3}$$

$$R_{l_1} = \frac{P_d - P_v}{S_l} \quad \text{Equation 5}$$

$$R_{l_2} = \frac{\overline{P}}{S_v} \quad \text{Equation 6}$$

Because the blood flows in right coronary artery at systole too, P, Qr, Rr, and Cr have the relationship as Equations 22 and 23.

$$C_r \frac{dP}{dt} + \frac{P - P_V}{R_r} = Q_r \quad 0 < t \le T_S \qquad \text{Equation 22}$$

$$C_r \frac{dP}{dt} + \frac{P - P_V}{Rr} = Q_r \quad T_S < t \le T (Q = Q_S + Q_d) \qquad \text{Equation 23}$$

Rr and Cr can be calculated by the function relationship between the area of aortic arch internal pressure curve P and the area of blood flow curve instead of adjusting R and C for coinciding those curves.

The reproducible R and C can be calculated by the function relationship between the areas.

$$\frac{k_2 A_S + A_d}{k_2 A_S - A_d} (P_S^* - P_d) \cdot = \frac{Sr}{Cr} \qquad \text{Equation 24}$$

The left side of Equation 24 is that the systolic carotid artery area is added to the diastolic carotid artery area, divided by the systolic aortic arch internal pressure curve area subtracted by the diastolic aortic arch internal pressure curve area, and multiplied by the blood pressure of the incisura point subtracted by that of the diastole. The left side of Equation 24 is same to the blood flow volume divided by the compliance.

In other words, when input signal is the area of the aortic arch internal pressure curve and output signal is the blood flow volume, the function relationship is $$k_2 A_S + A_d^* = f(k_2 As, Ad, P_S^*, P_d, Cr) Sr \qquad \text{Equation 25}$$

From Equation 25, the compliance Cr is $$C_r = \frac{k_2 A_S - A_d}{P_S^* - P_d} \cdot \frac{S_r}{k_2 A_S + A_d} \qquad \text{Equation 4}$$

And the resistance Rr is $$Rr = \frac{k_2 A_S + A_d}{Sr} \qquad \text{Equation 7}$$

Therefore, the changes of blood pressure, blood flow volume, and area of aortic arch internal pressure curve are sensitive to the arteriosclerosis of blood vessel, the seizure and spasm of blood vessel, the drug reaction, and the blood pressure changes.

Next, when the coronary artery is an elastic tube as a simple pipe with blood flow, the organic and the functional changes of the coronary artery are distinguished as the solution of fluid elastic function in the elastic tube with blood flow.

From FIG. 4, when the left coronary artery 42 and the right coronary artery 44 are a single pipe, the continuity equation and the motion equation are described as $$\frac{A}{\rho p w v^2} \cdot \frac{\partial P}{\partial t} + \frac{\partial Q}{\partial X} = 0 \qquad \text{Equation 26}$$

$$\frac{\rho}{A} \frac{\partial Q}{\partial t} = -\frac{\partial P}{\partial X} - \frac{8\mu\pi Q}{A^2} \qquad \text{Equation 27}$$

In Equation 26, pwv is the pulse wave velocity $$\left( pwv = \sqrt{\frac{A \cdot dP}{\rho \cdot dA}} \right),$$

P is a curve of blood pressure, Q is a curve of blood flow volume, µ is a viscosity, A is a cross-section area of blood vessel, and ρ is a density of blood.

Now, when $$\frac{\rho}{A} \frac{\partial Q}{\partial t}$$

is ignored, the integral on X is $$\frac{A}{\rho a^2} \frac{dP}{dt} + \frac{A^2 (P - P_V)}{8\pi \mu_p} = Q_d \qquad \text{Equation 28}$$

From Equation 28, Equations 29 and 30 are derived in the single elastic tube.

$$\frac{A}{\rho p w v^2} = C \qquad \text{Equation 29}$$

$$R = \frac{8\pi\mu}{A^2} \qquad \text{Equation 30}$$

On the other hand, according to Moesnsu Korteweg, because PWV=√(E/ρ)(h/d)=a(h/d), the elastic coefficient is E=ρ(d/h)PWV².

Consequently, because the elastic coefficient (i.e., the arterial stiffness) E is expressed as the elastic wave velocity a, E represents the organic change in coronary artery, but not related to the blood pressure change, the seizure, the spasm and the drug reaction in the coronary blood vessel.

Therefore, the arterial stiffness Asc (elastic coefficient) of coronary artery is obtained by eliminating A from C and R and then transformed as:

$$Asc = K_3 \frac{R^{0.25}}{CR} (1 - S) \qquad \text{Equation 31}$$

In Equation 31, S is S=f(PWV) and $K_3$ is a coefficient from clinics.

Next, in order to use the above mentioned indicators reflecting the property of coronary blood vessel and the characters of the bloodstream in clinics, the blood flow volume which flows to the coronary artery must be calculated.

Now, in order to clarify this issue, it is needed to consider as the left and right coronary arteries are distinguished each other.

First, when L is the length of right coronary and A is a cross-section area, as already known from hydraulics, in lineal pipe, the waveform of blood pressure is similar to the waveform of blood flow volume in one-dimensional flow of slurry fluid.

Based on the above facts, the equation of blood flow volume which flows in the right coronary artery can be made as below.

From the experimental result, the blood pressure curve of the right coronary artery is as the following.

The curves of systolic and diastolic blood pressures are integrated as:

$$k_2 A_s = \int_0^{Ts} k_2 P(t)\,dt \quad \text{Equation 32}$$

$$A_d = \int_{Ts}^{T} P(t)\,dt \quad \text{Equation 33}$$

In Equations 32 and 33, Ts is a systolic time, T is a period of heart beat, and $k_2$ is 0.7~0.75.

From Frank's law, among the pulse pressure, blood flow velocity, elastic wave velocity and blood density in right coronary artery, Equation 34 is established as:

$$\Delta P = \rho V a \quad \text{Equation 34}$$

where V is a blood flow velocity, a is a pulse wave propagation speed, $\rho$ is a blood density, and $\Delta P$ is a pulse pressure.

When the right coronary artery is a single elastic tube, Flank equation is converted to MS. Donald equation and the blood flow can be calculated as:

$$S_r = K_1 p R^2 (1-\upsilon^2)^{1/2} Pm (1+Ad/K_2 As)/(\rho a) \quad \text{Equation 2}$$

where $\upsilon$ is Poisson constant of blood vessel, R is a diameter of blood vessel, Pm is an average of blood pressure, K1 is a coefficient related to the blood flow volume flowed in the right coronary artery from the entrance of coronary artery and is 0.12~0.15, and K2 is a tissue internal coefficient and is 0.7~0.75.

$$Pm = (K_2 As + Ad)/R \quad \text{Equation 35}$$

Next, it is discussed that the blood flow volume flows in the left coronary artery.

In the left coronary artery, the blood flow is occurred by the stored potential energy in aorta during the diastole. For this reason, in a systolic aorta, the compliance of blood vessel is as a supplementary factor for inducing the blood flow in the coronary artery.

According to the mentioned Frank equation, $Svc=\Delta P \pi R^2 T/(2\rho a)$. In the present invention, when the systole of aortic arch is considered as a heart to supply blood to the coronary artery, the vascular blood flow volume is calculated with MS. Donald equation $Sv=KPm(1+Ad/As)$ and can be constructed as:

$$S_l = KA_d\left(\frac{t_* + \Delta t_d}{\Delta t_d}\right) \quad \text{Equation 1}$$

In Equation 1, Ad is area of the diastolic aortic arch internal pressure curve P, t* is time to 0 of first-order derived function.

On the other hand, the coefficient K is $$K = KA \cdot \sqrt{C_s} \quad \text{Equation 8}$$

$$= kA\left[(2mP_d + 1) \cdot \frac{\frac{A_d}{R} - n(P_*^2 - P_d^2)}{(P_* - P_d) + m(P_*^2 - P_d^2)} + 2nP_d\right]$$

In Equation 8, k is a coefficient related to a blood flow volume flowing from an entrance of the coronary artery to the left coronary artery and is 0.85~0.88, $A=\pi R^2$ is an equivalent area of the left coronary artery, $C_s$ is a compliance at systole, and m and n are Cope constants.

Tables 4 and 5 show the Cope constant on race and the systolic compliance on age.

TABLE 4

| | Cope Constant on Race | | | |
|---|---|---|---|---|
| | m | | n | |
| Race | $1/P_a$ | 1/mmHg | $ml/P_a$ | $ml/P_a$ |
| European | $-2.03 \times 10^{-5}$ | $-2.703 \times 10^{-3}$ | $3.36 \times 10^{-8}$ | $0.6445 \times 10^{-4}$ |
| Asian | $-2.5 \times 10^{-5}$ | $-3.0 \times 10^{-5}$ | $5.07 \times 10^{-8}$ | $0.9 \times 10^{-4}$ |

TABLE 5

| | Systolic Compliance on Age | | |
|---|---|---|---|
| Age | Normal | Morbid | *** |
| 40 years | $1.007 \pm 0.05$ | $0.917 \pm 0.08$ | $0.771 \pm 0.07$ |
| 50 years | $0.918 \pm 0.05$ | $0.817 \pm 0.09$ | $0.667 \pm 0.08$ |
| 60 years | $0.854 \pm 0.04$ | $0.772 \pm 0.09$ | $0.548 \pm 0.09$ |

Equation 1 is similar to MS. Donald equation and is exactly reflecting the diastolic blood flow volume of the left coronary artery. In the present invention, Equation 1 is confirmed by the experiment with six dogs.

In the experiment, using the Doppler catheter, the blood flow volume is measured in the proximal circumflex of left coronary artery at the blood vessel extension. The cuff pulse wave and the carotid artery pulse wave are used to make the aortic arch internal pressure curve. The blood flow volume is calculated by Equation 1 suggested in the present invention.

According to the experimental result, it is suggested that the blood flow volume measured by Doppler catheter shows to have high relationship with the blood flow volume calculated from the aortic arch internal pressure curve.

In the examined dog, the pulse is 35~207 beats/min, the diastolic average artery pressure is 16~60 mmHg, the blood flow volume 0.12~0.14 ml, and the cardiac cycles is 481.

The blood flow velocity calculated by Doppler method is obtained if the distribution of blood flow velocity measured by Doppler catheter forms the Poiseuille velocity distribution and the space maximum velocity equals to the half of the spectrum maximum velocity.

Next, the blood flow volume measured by an ultrasound Doppler is calculated from $S_c=AV$. A is the cross-section area of the proximal circumflex of left coronary artery measured from the angiograph and V is the blood flow velocity.

The Doppler used to draw the blood flow curve is the Doppler Blood Vessel Forming Guide-wire Type Blood Flow Volume System with a Blood Flow Velocimetry for spectrum analysis.

The length of Guide-wire is 175 cm, the diameter is 18 inch, and the ultrasound Doppler type catheter has one end with a 12 MHz piezoelectric ultrasound sensor.

The equation for the blood flow volume of left coronary artery has ±6% error of experimentally measured values.

Using the same method, after experimenting in the right coronary artery, the result is follows: $Sc=1.21S*c-0.21$, $\gamma^2=0.86$, and $Se=3.98ff$.

Now, the above equations are integrated from Ts to T.

At this time, because Pv is much smaller than P, if Pv is ignored, $$S_{cv} = \int_{T_s}^{T} Q_{in} \, dt,$$

$$\int_{T_s}^{T} P \, dt = A_d,$$

$$CP|_{T_s}^{T} = C(P_* - P_d)$$

Equation 36

Equation 37

If the related equations are substituted, the result is $$C(P_* - P_d) + \frac{A_d}{R} = S_{cv}$$

Equation 37

In Equation 37, P* is the blood pressure of the incinura point and is $$P_* = P_d + p\frac{h_1}{h_2}(P_s - P_d)$$

Equation 38

On the other hand, R=(As+Ad)/Scl, Scl is the blood flow volume of left coronary artery.

Next, the blood flow velocity in the aorta is calculated.

The slope of the aortic arch internal pressure curve by invasive testing method is much different from that of the aortic arch internal pressure curve by noninvasive testing method at systole in one man.

However, the slope of the curves from the average blood pressure point to the diastolic end point shows a high relationship.

The relationship obtained from the 24 examinees is as follows:

Grad $Hc$=0.918Grad $Hn$+0.024, $\gamma^2$=0.92, $Se$=1.68$f$  Equation 39

In Equation 39, Grad Hc is the slope of the aortic arch internal pressure curve by invasive testing method and Grad Hn is the slope of the aortic arch internal pressure curve by noninvasive testing method.

On the other hand, if the blood flow in blood vessel is assumed as a Newtonian fluid with one-dimensional motion, the blood flow is considered as a fluid motion in terms of Euler because the blood flow is uniform by the mean of average S.

In other words, $V_1$=(dx/dt)$x_1$ at a point x1 of artery.

On the other hand, in the aortic arch internal pressure curve, the pulse wave is nearly linear on the change of pressure from the average point of artery pulse pressure to the diastolic end point and the follow equation is possible.

$$\left(\frac{dp}{dt}\right)DW = \frac{P(x_1, t_2) - P(x_1, t_1)}{t_2 - t_1} = A_0 V_0 / C$$

Equation 40

In Equation 40, $V_0$ is the average velocity of blood flow during the diastole and $t_1$ and $t_2$ are two time points in the diastole period.

From above mentioned, in the left coronary artery,

Blood flow velocity $V_1$ is $$V_l = \frac{C_l}{A_0}\left(\frac{dp}{dt}\right)_{DW}$$

Equation 11

The compliance of blood vessel $C_l$ is $$C_l = \frac{\left(S_l - \frac{A_d}{R_l}\right)}{(P_* - P_d)}$$

Equation 3

The resistance of blood flow $R_{l1}$ is $$R_{l_1} = \frac{P_d - P_v}{S_l}$$

Equation 5

The resistance of blood flow $R_{l2}$ is $$R_{l_2} = \frac{\overline{P}}{S_v}$$

Equation 6

The stiffness of artery $A_{sl}$ is $$As_l = K_3 \frac{R_{l_1}^{0.25}}{C_l R_{l_1}}(1 - S_l)$$

Equation 9

The blood flow volume $S_l$ is $$S_l = KA_d\left(\frac{t_* + \Delta t_d}{\Delta t_d}\right)$$

Equation 1

On the other hand, in the right coronary artery,

The compliance of blood vessel $C_l$ is $$C_r = \frac{k_2 A_S - A_d}{P_S^* - P_d} \cdot \frac{S_r}{k_2 A_S + A_{d_i}}$$

Equation 4

The resistance of blood flow $R_r$ is $$Rr = \frac{k_2 A_S + A_d}{Sr}$$

Equation 7

The blood flow velocity $V_r$ is $$Vr = \frac{C_r}{A_0}\left(\frac{dp}{dt}\right)_{DW}$$

Equation 12

The artery stiffness $A_{sr}$ is $$Asr = K_3 \frac{Rr^{0.25}}{CrRr}(1 - S_r)$$ Equation 10

The blood flow $S_r$ is $$S_r = K_pR^2(1-\upsilon^2)^{1/2}Pm(1+Ad/K_2As)/(\rho a)$$ Equation 2

Finally, the cardiovascular analyzer of the present invention is clinically tested to the patients in University Hospital in Korea and the results are described.

The following clinical examinations are tested to the 34 patients with the coronary artery disease-like who are measured with angiography and the results are showed in Tables 6 and 7.

TABLE 6

Population Statistics of Patients (n = 34)

| Parameter | Result |
| --- | --- |
| Age (year) | 60.8 ± 11.0 |
| No. of Male (%) | 18(52.9) |
| No. of Clinical Diagnosis (%) | |
| No. of Stable Angina (%) | 34(100) |
| Left Ventricular Ejection Rate (%) | 67.7 ± 7.6 |
| No. of Previous Myocardial Infection (%) | 1(2.9) |
| No. of Severe Coronary Artery Disease (Stenosis >50%) (%) | 18(52.9) |

TABLE 7

Device Sensitivity and Characteristics for Detecting Severe Coronary Artery Disease

| | Mild Coronary Artery Disease | Severe Coronary Artery Disease | Total |
| --- | --- | --- | --- |
| Negative | 6 | 4 | 10 |
| Low Possibility | 7 | 1 | 8 |
| High Possibility | 0 | 4 | 4 |
| Positive | 3 | 7 | 10 |
| Total | 16 | 16 | 32 |

In Tables 6 and 7, severe coronary artery disease (CAD) shows above 50% of stenosis, at least, in one of the major coronary arteries by angiography.

When severe coronary artery disease is positive result, it is certainly the category of high possibility, but the categories of low possibility and negative are divided into several uncertain results of severe coronary artery disease.

Consequently, the cardiovascular analyzer of the present invention shows considerably excellent sensitivity and diagnostic characteristics for diagnosis of severe coronary artery diseases more than that of the other screen diagnosis instruments such as electrocardiography and ultrasound heart diagnosis device.

In addition, the cardiovascular analyzer of the present invention has some advantages such as the measuring time, the noninvasive property, and the adaptability to all most patient with the unable to walk and/or the side effect of dobutamine stress.

The cardiovascular analyzer of the present invention shows considerably excellent sensitivity and diagnostic characteristics for diagnosis of severe coronary artery diseases more than that of the other screen diagnosis instruments such as electrocardiography and ultrasound heart diagnosis device, and also shows the diagnosis of the organic and functional states which are not detected by angiography. Consequently, the cardiovascular analyzer of the present invention has a very high industrial applicability because of the early diagnosis of the several cardiovascular incurable diseases and the selection of the cardiovascular surgery examinee by the noninvasive testing method.

The invention claimed is:

1. A cardiovascular analyzer comprising:
 a bio-signal measurement system including a bio-signal measuring sensor unit which comprises an electrocardiogram (ECG) sensor, a phonocardiogram (PCG) sensor and one or more accelerated plethysmogram (APG) sensors, and a bio-signal reception and process unit which is connected to each of the sensors of the bio-signal measuring sensor unit for receiving and processing bio-signals measured by the sensors; and
 an analysis indicator calculation system including a main processing unit which is connected to the bio-signal reception and process unit for communicating and calculating biodynamic indicators of a coronary artery from the bio-signals, an input unit which is connected to the main processing unit for receiving control commends of user, and an output unit which is connected to the main processing unit for displaying the calculated results,
 wherein the main processing unit is configured to synthesizes an aortic arch internal pressure curve P from the bio-signals measured by the bio-signal measurement system and to calculates the biodynamic indicators from an area of the aortic arch internal pressure curve P.

2. The cardiovascular analyzer of claim 1,
 wherein the bio-signal reception and process unit comprises:
 a microcontroller which controls to process the bio-signals received from the bio-signal measuring unit and to transmit processed bio-signals to the main processing unit;
 a multi-signal selector which selects one of the bio-signals received from the ECG sensor, the PCG sensor and the APG sensors by a control signal of the microcontroller;
 a noise eliminator and signal amplifier which eliminates noises and/or controls amplification degree of the bio-signal selected by the multi-signal sensor by a control signal of the microcontroller;
 a signal switcher which receives the bio-signals from the noise eliminator and signal amplifier and selects one of the bio-signals to meet the control commands of the input unit or of embedded program in the main processing unit by a control signal of the microcontroller;
 a sample holder which samples and holds the bio-signal selected by the signal switcher by a control signal of the microcontroller; and
 an A/D converter which converts a holding bio-signal of the sample holder to a digital bio-signal and sends to the microcontroller by a control signal of the microcontroller.

3. The cardiovascular analyzer of claim 2,
 wherein each of the APG sensors is configured to obtain an APG waveform by sensing a pulse wave due to the pulsatory motion of an artery; and
 wherein the bio-signal measurement system is configured to obtains an ECG waveform, a PCG waveform and the APG waveform synchronously by the bio-signal measuring sensor unit.

4. The cardiovascular analyzer of claim 3,
wherein one of the APG sensors is a cuff pulse wave sensor being a cuff sphygmomanometer equipped with a pressure sensor to sense the pulse wave.

5. The cardiovascular analyzer of claim 4,
wherein the cuff pulse wave sensor comprises a rubber hose which is connected to an air pouch of the cuff sphygmomanometer, a branch hose which is connected to the rubber tube, and an adaptor which is connected to an exit of the branch hose; and
wherein the adaptor is assembled to the pressure sensor to sense the pulse wave.

6. The cardiovascular analyzer of claim 1,
wherein each of the APG sensors is configured to obtain an APG waveform by sensing a pulse wave due to the pulsatory motion of an artery; and
wherein the bio-signal measurement system is configured to obtains an ECG waveform, a PCG waveform and the APG waveform synchronously by the bio-signal measuring sensor unit.

7. The cardiovascular analyzer of claim 6,
wherein one of the APG sensors is a cuff pulse wave sensor being a cuff sphygmomanometer equipped with a pressure sensor to sense the pulse wave.

8. The cardiovascular analyzer of claim 7,
wherein the cuff pulse wave sensor comprises a rubber hose which is connected to a air pouch of the cuff sphygmomanometer, a branch hose which is connected to the rubber tube, and an adaptor which is connected to an exit of the branch hose; and
wherein the adaptor is connected to the pressure sensor sensing the pulse wave.

9. The cardiovascular analyzer of claim 1,
wherein the main processing unit is programmed to carry out the steps of:
(1) ordering the bio-signal measurement system to measure the bio-signals and receiving the bio-signals from the bio-signal measurement system;
(2) analyzing waveforms from the received bio-signals and synthesizing the aortic arch internal pressure curve P from the analyzed waveforms; and
(3) calculating the biodynamic indicators from the area of the synthesized aortic arch internal pressure curve P and displaying the results of cardiovascular analysis.

10. The cardiovascular analyzer of claim 9,
wherein analyzing waveforms from the received bio-signals in step 2 comprises:
finding feature points, including systolic upstroke point, systolic peak point, incisura point, diastolic peak point and diastolic end point, of the aortic arch internal pressure curve P by analyzing ECG signals and PCG signals measured by the ECG sensor and the PCG sensor of the bio-signals measurement system, respectively;
finding high frequency elements of the aortic arch internal pressure curve P by analyzing Cuff-APG pulse waves measured by a cuff pulse wave sensor, as one of the APG sensors of the bio-signals measurement system, which is pressurized above the systolic blood pressure;
finding low frequency elements of the aortic arch internal pressure curve P by analyzing Cuff-APG pulse waves measured by the cuff pulse wave sensor which is depressurized below the diastolic blood pressure; and
finding a time-frequency intensity of the aortic arch internal pressure curve P by analyzing APG pulse waves of the left and right carotid arteries measured by a carotid artery pulse wave sensor as one of the APG sensors of the bio-signals measurement system, and
wherein the synthesis of the aortic arch internal pressure curve P is based on basic information including the analyzed data of Cuff-APG pulse waves at the systole and the diastole and the analyzed data of APG pulse waves of the left and right carotid arteries.

11. The cardiovascular analyzer of claim 10,
wherein the main processing unit is further programmed to carry out the steps of:
displaying an initial screen including a search menu window, a patient information window, a test and diagnosis window and a test result window in the output unit before step 1;
receiving and saving the information of patient if a registration command for new patient is received in the initial screen, otherwise, receiving an opening command to open a registered patient file;
displaying a patient list in the registered patient file on the test result window if the opening command is received and receiving a signal for selecting a patient and new information of the selected patient, otherwise, displaying the initial screen continuously; and
displaying the information of new patient or the selected patient on the patient information window and receiving a test and diagnosis command, and
wherein the information of new patient or the selected patient comprises a personally identified information and body information including one or more of height, weight, blood pressure and race.

12. The cardiovascular analyzer of claim 11,
wherein performance of step 1 by the main processing unit further includes the steps of:
(1-1) displaying a command selection window for the bio-signal measurement if a test command is received from the test and diagnosis window, otherwise, keeping the previous state;
(1-2-1) receiving ECG, PCG and high frequency APG waveforms measured by the ECG sensor, the PCG sensor and a pressurized cuff pulse wave sensor as one of the APG sensors of the bio-signal measuring sensor unit and displaying on the test result window if the measurement command of a systolic pulse wave is received from the command selection window, otherwise, keeping the previous state as a standby step for receiving a bio-signal measurement command;
(1-2-2) receiving ECG, PCG and low frequency APG waveforms measured by the ECG sensor, the PCG sensor and a depressurized cuff pulse wave sensor as one of the APG sensors of the bio-signal measuring sensor unit and displaying on the test result window if the measurement command of a diastolic pulse wave is received from the command selection window, otherwise, keeping the previous state as a standby step for receiving a bio-signal measurement command;
(1-2-3) receiving ECG, PCG and left carotid artery APG waveforms measured by the ECG sensor, the PCG sensor and a carotid artery pulse wave sensor as one of the APG sensors of the bio-signal measuring sensor unit and displaying on the test result window if the measurement command of the left carotid artery is received from the command selection window, otherwise, keeping the previous state as a standby step for receiving a bio-signal measurement command;
(1-2-4) receiving ECG, PCG and right carotid artery APG waveforms measured by the ECG sensor, the PCG sensor and a carotid artery pulse wave sensor as one of the APG sensors of the bio-signal measuring sensor unit and displaying on the test result window if the measurement command of the right carotid artery is received from the command selection window, otherwise, keeping the previous state as a standby step for receiving a bio-signal measurement command;

(1-2-5) receiving ECG, PCG and femoral artery APG waveforms measured by the ECG sensor, the PCG sensor and a femoral artery pulse wave sensor as one of the APG sensors of the bio-signal measuring sensor unit and displaying on the test result window if the measurement command of the femoral artery is received from the command selection window, otherwise, keeping the previous state as a standby step for receiving a bio-signal measurement command; and (1-3) capturing a screen showing a selected ideal waveform among the waveforms displayed on the test result window and saving if a waveform selection command is received after each of steps 1-2-1 to 1-2-5, otherwise, keeping the measurement and displaying the measured waveforms continuously.

13. The cardiovascular analyzer of claim 12,
wherein analyzing waveforms from the received bio-signals and synthesizing the aortic arch internal pressure curve P from the analyzed waveforms in step 2 comprise:

(2-1) displaying an analysis menu window if an analysis command is received from the test and diagnosis window, otherwise, keeping the previous step;

(2-2) analyzing automatically feature points of the saved ECG, PCG and high frequency APG waveforms and displaying on the test result window if a systolic bio-signal analysis command is received from the analysis menu window, otherwise, keeping the previous step;

(2-3) analyzing automatically feature points of the saved ECG, PCG and low frequency APG waveforms and displaying on the test result window if a diastolic bio-signals analysis command is received from the analysis menu window, otherwise, keeping the previous step;

(2-4) displaying the saved left and right carotid artery waveforms on the test result window if a synthesized signal analysis command is received from the analysis menu window, otherwise, keeping the previous step;

(2-5) displaying enlarged waveforms analyzed in a selected interval on a lower left corner of the test result window if a detail analysis interval is selected in the left and right carotid artery waveforms showing on the test result window, otherwise, keeping the previous step; and (2-6) displaying an aortic arch internal pressure curve, which is synthesized with the information including the saved ECG, PCG and APG waveforms, in a place clicked on the test results window if a vacant space of a lower right corner of the test results window is clicked after the sequential displays of the enlarged left and right carotid artery waveforms on the lower left corner of the test results window, otherwise, keeping the previous step.

14. The cardiovascular analyzer of claim 13,
wherein each of steps 2-2, 2-3, and 2-4 causes the main processing unit to return to step 1-1 if a test command is received from the result and diagnosis window after displaying each waveform on the test result window, and wherein if the test command is not received, each of steps 2-2, 2-3, and 2-4 is followed by the subsequent step.

15. The cardiovascular analyzer of claim 13,
wherein step 3 comprises:
(3-1) displaying a result menu window and a output device icon if a result display command is received from the test and diagnosis window, otherwise, displaying a patient list in the registered patient file on the test result window and receiving a signal for selecting a patient and new information of the selected patient till receiving a command;

(3-2) displaying a selected menu result if one is selected on the result menu window, otherwise, keeping step 3-1; and (3-3) outputting the selected menu result if an output command is received from the output device icon after displaying the selected menu result, otherwise, keeping step 3-2.

16. The cardiovascular analyzer of claim 15,
wherein the result menu window comprises a Compliance-Resistance (C-R) chart; and
wherein the C-R chart is divided into sectors to show the coronary artery states according to the clinical results and is dotted to show the states of the left and right coronary arteries of an examinee.

17. The cardiovascular analyzer of claim 9,
wherein step 3 comprises:
calculating blood flow volumes $S_l$ and $S_r$ of the left and right coronary arteries from basic data including the area of the aortic arch internal pressure curve P;

calculating compliances $C_l$ and $C_r$ and blood flow resistances $R_l$ and $R_r$ of the left and right coronary arteries from the aortic arch internal pressure curve P and the blood flow volumes $S_l$ and $S_r$ of the left and right coronary arteries; and transmitting the results of cardiovascular analysis to the output unit for showing the calculated compliances $C_l$ and $C_r$ and the calculated blood flow resistances $R_l$ and $R_r$ of the left and right coronary arteries on one C-R chart.

18. The cardiovascular analyzer of claim 17,
wherein analyzing waveforms from the received bio-signals in step 2 comprises:
finding feature points, including systolic upstroke point, systolic peak point, incisura point, diastolic peak point and diastolic end point, of the aortic arch internal pressure curve P by analyzing ECG signals and PCG signals measured by the ECG sensor and the PCG sensor of the bio-signals measurement system, respectively;

finding high frequency elements of the aortic arch internal pressure curve P by analyzing Cuff-APG pulse waves measured by a cuff pulse wave sensor, as one of the APG sensors of the bio-signals measurement system, which is pressurized above the systolic blood pressure;

finding low frequency elements of the aortic arch internal pressure curve P by analyzing Cuff-APG pulse waves measured by the cuff pulse wave sensor which is depressurized below the diastolic blood pressure; and finding a time-frequency intensity of the aortic arch internal pressure curve P by analyzing APG pulse waves of the left and right carotid arteries measured by a carotid artery pulse wave sensor as one of the APG sensors of the bio-signals measurement system, and wherein the synthesis of the aortic arch internal pressure curve P is based on basic information including the analyzed data of Cuff-APG pulse waves at the systole and the diastole and the analyzed data of APG pulse waves of the left and right carotid arteries.

19. The cardiovascular analyzer of claim 18,
wherein the main processing unit is further programmed to carry out the steps of:

displaying an initial screen including a search menu window, a patient information window, a test and diagnosis window and a test result window in the output unit before step 1;

receiving and saving the information of patient if a registration command for new patient is received in the initial screen, otherwise, receiving an opening command to open a registered patient file;

displaying a patient list in the registered patient file on the test result window if the opening command is received and receiving a signal for selecting a patient and new information of the selected patient, otherwise, displaying the initial screen continuously; and displaying the information of new patient or the selected patient on the patient information window and receiving a test and diagnosis command, and wherein the information of new patient or the selected patient comprises a personally identified information and body information including one or more of height, weight, blood pressure and race.

20. The cardiovascular analyzer of claim 19, wherein performance of step 1 by the main processing unit further includes the steps of:

(1-1) displaying a command selection window for the bio-signal measurement if a test command is received from the test and diagnosis window, otherwise, keeping the previous state;

(1-2-1) receiving ECG, PCG and high frequency APG waveforms measured by the ECG sensor, the PCG sensor and a pressurized cuff pulse wave sensor as one of the APG sensors of the bio-signal measuring sensor unit and displaying on the test result window if the measurement command of a systolic pulse wave is received from the command selection window, otherwise, keeping the previous state as a standby step for receiving a bio-signal measurement command;

(1-2-2) receiving ECG, PCG and low frequency APG waveforms measured by the ECG sensor, the PCG sensor and a depressurized cuff pulse wave sensor as one of the APG sensors of the bio-signal measuring sensor unit and displaying on the test result window if the measurement command of a diastolic pulse wave is received from the command selection window, otherwise, keeping the previous state as a standby step for receiving a bio-signal measurement command;

(1-2-3) receiving ECG, PCG and left carotid artery APG waveforms measured by the ECG sensor, the PCG sensor and a carotid artery pulse wave sensor as one of the APG sensors of the bio-signal measuring sensor unit and displaying on the test result window if the measurement command of the left carotid artery is received from the command selection window, otherwise, keeping the previous state as a standby step for receiving a bio-signal measurement command;

(1-2-4) receiving ECG, PCG and right carotid artery APG waveforms measured by the ECG sensor, the PCG sensor and a carotid artery pulse wave sensor as one of the APG sensors of the bio-signal measuring sensor unit and displaying on the test result window if the measurement command of the right carotid artery is received from the command selection window, otherwise, keeping the previous state as a standby step for receiving a bio-signal measurement command;

(1-2-5) receiving ECG, PCG and femoral artery APG waveforms measured by the ECG sensor, the PCG sensor and a femoral artery pulse wave sensor as one of the APG sensors of the bio-signal measuring sensor unit and displaying on the test result window if the measurement command of the femoral artery is received from the command selection window, otherwise, keeping the previous state as a standby step for receiving a bio-signal measurement command; and (1-3) capturing a screen showing a selected ideal waveform among the waveforms displayed on the test result window and saving if a waveform selection command is received after each of steps 1-2-1 to 1-2-5, otherwise, keeping the measurement and displaying the measured waveforms continuously.

21. The cardiovascular analyzer of claim 20, wherein analyzing waveforms from the received bio-signals and synthesizing the aortic arch internal pressure curve P from the analyzed waveforms in step 2 comprise:

(2-1) displaying an analysis menu window if an analysis command is received from the test and diagnosis window, otherwise, keeping the previous step;

(2-2) analyzing automatically feature points of the saved ECG, PCG and high frequency APG waveforms and displaying on the test result window if a systolic bio-signal analysis command is received from the analysis menu window, otherwise, keeping the previous step;

(2-3) analyzing automatically feature points of the saved ECG, PCG and low frequency APG waveforms and displaying on the test result window if a diastolic bio-signals analysis command is received from the analysis menu window, otherwise, keeping the previous step;

(2-4) displaying the saved left and right carotid artery waveforms on the test result window if a synthesized signal analysis command is received from the analysis menu window, otherwise, keeping the previous step;

(2-5) displaying enlarged waveforms analyzed in a selected interval on a lower left corner of the test result window if a detail analysis interval is selected in the left and right carotid artery waveforms showing on the test result window, otherwise, keeping the previous step; and (2-6) displaying an aortic arch internal pressure curve, which is synthesized with the information including the saved ECG, PCG and APG waveforms, in a place clicked on the test results window if a vacant space of a lower right corner of the test results window is clicked after the sequential displays of the enlarged left and right carotid artery waveforms on the lower left corner of the test results window, otherwise, keeping the previous step.

22. The cardiovascular analyzer of claim 21, wherein each of steps 2-2, 2-3, and 2-4 causes the main processing unit to return to step 1-1 if a test command is received from the result and diagnosis window after displaying each waveform on the test result window, and wherein if the test command is not received, each of steps 2-2, 2-3, and 2-4 is followed by the subsequent step.

23. The cardiovascular analyzer of claim 21, wherein step 3 comprises:

(3-1) displaying a result menu window and a output device icon if a result display command is received from the test and diagnosis window, otherwise, displaying a patient list in the registered patient file on the test result window and receiving a signal for selecting a patient and new information of the selected patient till receiving a command;

(3-2) displaying a selected menu result if one is selected on the result menu window, otherwise, keeping step 3-1; and (3-3) outputting the selected menu result if an output command is received from the output device icon after displaying the selected menu result, otherwise, keeping step 3-2.

24. The cardiovascular analyzer of claim 23,
wherein the result menu window comprises a Compliance-Resistance (C-R) chart; and
wherein the C-R chart is divided into sectors to show the coronary artery states according to the clinical results and
is dotted to show the states of the left and right coronary arteries of an examinee.

25. The cardiovascular analyzer of claim 17,
wherein step 3 further comprises:
calculating arterial stiffness $As_l$ and $As_r$ of the left and right coronary arteries from the blood flow volumes $S_l$ and $S_r$, the compliances $C_l$ and $C_r$ and the blood flow resistances $R_l$ and $R_r$ of the left and right coronary arteries and transmitting to the output unit.

26. The cardiovascular analyzer of claim 25,
wherein the arterial stiffness $As_l$ and $As_r$ of the left and right coronary arteries are calculated by the equations of:
the arterial stiffness $As_l$ of the left coronary artery is $$As_l = K_3 \frac{R_{l_1}^{0.25}}{C_l R_{l_1}} (1 - S_l)$$

and the arterial stiffness $As_r$ of the right coronary artery is $$Asr = K_3 \frac{Rr^{0.25}}{CrRr} (1 - S_r)$$

where $K_3$ is a coefficient derived from the clinics and is 0.7~0.89.

27. The cardiovascular analyzer of claim 26,
wherein analyzing waveforms from the received bio-signals in step 2 comprises:
finding feature points, including systolic upstroke point, systolic peak point, incisura point, diastolic peak point and diastolic end point, of the aortic arch internal pressure curve P by analyzing ECG signals and PCG signals measured by the ECG sensor and the PCG sensor of the bio-signals measurement system, respectively;
finding high frequency elements of the aortic arch internal pressure curve P by analyzing Cuff-APG pulse waves measured by a cuff pulse wave sensor, as one of the APG sensors of the bio-signals measurement system, which is pressurized above the systolic blood pressure;
finding low frequency elements of the aortic arch internal pressure curve P by analyzing Cuff-APG pulse waves measured by the cuff pulse wave sensor which is depressurized below the diastolic blood pressure; and
finding a time-frequency intensity of the aortic arch internal pressure curve P by analyzing APG pulse waves of the left and right carotid arteries measured by a carotid artery pulse wave sensor as one of the APG sensors of the bio-signals measurement system, and
wherein the synthesis of the aortic arch internal pressure curve P is based on basic information including the analyzed data of Cuff-APG pulse waves at the systole and the diastole and the analyzed data of APG pulse waves of the left and right carotid arteries.

28. The cardiovascular analyzer of claim 27,
wherein the main processing unit is further programmed to carry out the steps of:
displaying an initial screen including a search menu window, a patient information window, a test and diagnosis window and a test result window in the output unit before step 1;
receiving and saving the information of patient if a registration command for new patient is received in the initial screen, otherwise, receiving an opening command to open a registered patient file;
displaying a patient list in the registered patient file on the test result window if the opening command is received and receiving a signal for selecting a patient and new information of the selected patient, otherwise, displaying the initial screen continuously; and
displaying the information of new patient or the selected patient on the patient information window and receiving a test and diagnosis command, and
wherein the information of new patient or the selected patient comprises a personally identified information and body information including one or more of height, weight, blood pressure and race.

29. The cardiovascular analyzer of claim 28,
wherein performance of step 1 by the main processing unit further includes the steps of:
(1-1) displaying a command selection window for the bio-signal measurement if a test command is received from the test and diagnosis window, otherwise, keeping the previous state;
(1-2-1) receiving ECG, PCG and high frequency APG waveforms measured by the ECG sensor, the PCG sensor and a pressurized cuff pulse wave sensor as one of the APG sensors of the bio-signal measuring sensor unit and displaying on the test result window if the measurement command of a systolic pulse wave is received from the command selection window, otherwise, keeping the previous state as a standby step for receiving a bio-signal measurement command;
(1-2-2) receiving ECG, PCG and low frequency APG waveforms measured by the ECG sensor, the PCG sensor and a depressurized cuff pulse wave sensor as one of the APG sensors of the bio-signal measuring sensor unit and displaying on the test result window if the measurement command of a diastolic pulse wave is received from the command selection window, otherwise, keeping the previous state as a standby step for receiving a bio-signal measurement command;
(1-2-3) receiving ECG, PCG and left carotid artery APG waveforms measured by the ECG sensor, the PCG sensor and a carotid artery pulse wave sensor as one of the APG sensors of the bio-signal measuring sensor unit and displaying on the test result window if the measurement command of the left carotid artery is received from the command selection window, otherwise, keeping the previous state as a standby step for receiving a bio-signal measurement command;
(1-2-4) receiving ECG, PCG and right carotid artery APG waveforms measured by the ECG sensor, the PCG sensor and a carotid artery pulse wave sensor as one of the APG sensors of the bio-signal measuring sensor unit and displaying on the test result window if the measurement command of the right carotid artery is received from the command selection window, otherwise, keeping the previous state as a standby step for receiving a bio-signal measurement command;

(1-2-5) receiving ECG, PCG and femoral artery APG waveforms measured by the ECG sensor, the PCG sensor and a femoral artery pulse wave sensor as one of the APG sensors of the bio-signal measuring sensor unit and displaying on the test result window if the measurement command of the femoral artery is received from the command selection window, otherwise, keeping the previous state as a standby step for receiving a bio-signal measurement command; and (1-3) capturing a screen showing a selected ideal waveform among the waveforms displayed on the test result window and saving if a waveform selection command is received after each of steps 1-2-1 to 1-2-5, otherwise, keeping the measurement and displaying the measured waveforms continuously.

30. The cardiovascular analyzer of claim 29,
wherein analyzing waveforms from the received bio-signals and synthesizing the aortic arch internal pressure curve P from the analyzed waveforms in step 2 comprise:

(2-1) displaying an analysis menu window if an analysis command is received from the test and diagnosis window, otherwise, keeping the previous step;

(2-2) analyzing automatically feature points of the saved ECG, PCG and high frequency APG waveforms and displaying on the test result window if a systolic bio-signal analysis command is received from the analysis menu window, otherwise, keeping the previous step;

(2-3) analyzing automatically feature points of the saved ECG, PCG and low frequency APG waveforms and displaying on the test result window if a diastolic bio-signals analysis command is received from the analysis menu window, otherwise, keeping the previous step;

(2-4) displaying the saved left and right carotid artery waveforms on the test result window if a synthesized signal analysis command is received from the analysis menu window, otherwise, keeping the previous step;

(2-5) displaying enlarged waveforms analyzed in a selected interval on a lower left corner of the test result window if a detail analysis interval is selected in the left and right carotid artery waveforms showing on the test result window, otherwise, keeping the previous step; and (2-6) displaying an aortic arch internal pressure curve, which is synthesized with the information including the saved ECG, PCG and APG waveforms, in a place clicked on the test results window if a vacant space of a lower right corner of the test results window is clicked after the sequential displays of the enlarged left and right carotid artery waveforms on the lower left corner of the test results window, otherwise, keeping the previous step.

31. The cardiovascular analyzer of claim 30,
wherein step 3 comprises:

(3-1) displaying a result menu window and a output device icon if a result display command is received from the test and diagnosis window, otherwise, displaying a patient list in the registered patient file on the test result window and receiving a signal for selecting a patient and new information of the selected patient till receiving a command;

(3-2) displaying a selected menu result if one is selected on the result menu window, otherwise, keeping step 3-1; and (3-3) outputting the selected menu result if an output command is received from the output device icon after displaying the selected menu result, otherwise, keeping step 3-2.

32. The cardiovascular analyzer of claim 31,
wherein the result menu window comprises a Compliance-Resistance (C-R) chart; and
wherein the C-R chart is divided into sectors to show the coronary artery states according to the clinical results and
is dotted to show the states of the left and right coronary arteries of an examinee.

33. The cardiovascular analyzer of claim 30,
wherein each of steps 2-2, 2-3, and 2-4 causes the main processing unit to return to step 1-1 if a test command is received from the result and diagnosis window after displaying each waveform on the test result window, and wherein if the test command is not received, each of steps 2-2, 2-3, and 2-4 is followed by the subsequent step.

34. The cardiovascular analyzer of claim 25,
wherein analyzing waveforms from the received bio-signals in step 2 comprises:
finding feature points, including systolic upstroke point, systolic peak point, incisura point, diastolic peak point and diastolic end point, of the aortic arch internal pressure curve P by analyzing ECG signals and PCG signals measured by the ECG sensor and the PCG sensor of the bio-signals measurement system, respectively;
finding high frequency elements of the aortic arch internal pressure curve P by analyzing Cuff-APG pulse waves measured by a cuff pulse wave sensor, as one of the APG sensors of the bio-signals measurement system, which is pressurized above the systolic blood pressure;
finding low frequency elements of the aortic arch internal pressure curve P by analyzing Cuff-APG pulse waves measured by the cuff pulse wave sensor which is depressurized below the diastolic blood pressure; and
finding a time-frequency intensity of the aortic arch internal pressure curve P by analyzing APG pulse waves of the left and right carotid arteries measured by a carotid artery pulse wave sensor one of as the APG sensors of the bio-signals measurement system, and
wherein the synthesis of the aortic arch internal pressure curve P is based on basic information including the analyzed data of Cuff-APG pulse waves at the systole and the diastole and the analyzed data of APG pulse waves of the left and right carotid arteries.

35. The cardiovascular analyzer of claim 34,
wherein the main processing unit is further programmed to carry out the steps of:
displaying an initial screen including a search menu window, a patient information window, a test and diagnosis window and a test result window in the output unit before step 1;
receiving and saving the information of patient if a registration command for new patient is received in the initial screen, otherwise, receiving an opening command to open a registered patient file;
displaying a patient list in the registered patient file on the test result window if the opening command is received and receiving a signal for selecting a patient and new information of the selected patient, otherwise, displaying the initial screen continuously; and
displaying the information of new patient or the selected patient on the patient information window and receiving a test and diagnosis command, and
wherein the information of new patient or the selected patient comprises a personally identified information and body information including one or more of height, weight, blood pressure and race.

36. The cardiovascular analyzer of claim 35,
wherein performance of step 1 by the main processing unit further includes the steps of:
(1-1) displaying a command selection window for the bio-signal measurement if a test command is received from the test and diagnosis window, otherwise, keeping the previous state;
(1-2-1) receiving ECG, PCG and high frequency APG waveforms measured by the ECG sensor, the PCG sensor and a pressurized cuff pulse wave sensor as one of the APG sensors of the bio-signal measuring sensor unit and displaying on the test result window if the measurement command of a systolic pulse wave is received from the command selection window, otherwise, keeping the previous state as a standby step for receiving a bio-signal measurement command;
(1-2-2) receiving ECG, PCG and low frequency APG waveforms measured by the ECG sensor, the PCG sensor and a depressurized cuff pulse wave sensor as one of the APG sensors of the bio-signal measuring sensor unit and displaying on the test result window if the measurement command of a diastolic pulse wave is received from the command selection window, otherwise, keeping the previous state as a standby step for receiving a bio-signal measurement command;
(1-2-3) receiving ECG, PCG and left carotid artery APG waveforms measured by the ECG sensor, the PCG sensor and a carotid artery pulse wave sensor as one of the APG sensors of the bio-signal measuring sensor unit and displaying on the test result window if the measurement command of the left carotid artery is received from the command selection window, otherwise, keeping the previous state as a standby step for receiving a bio-signal measurement command;
(1-2-4) receiving ECG, PCG and right carotid artery APG waveforms measured by the ECG sensor, the PCG sensor and a carotid artery pulse wave sensor as one of the APG sensors of the bio-signal measuring sensor unit and displaying on the test result window if the measurement command of the right carotid artery is received from the command selection window, otherwise, keeping the previous state as a standby step for receiving a bio-signal measurement command;
(1-2-5) receiving ECG, PCG and femoral artery APG waveforms measured by the ECG sensor, the PCG sensor and a femoral artery pulse wave sensor as one of the APG sensors of the bio-signal measuring sensor unit and displaying on the test result window if the measurement command of the femoral artery is received from the command selection window, otherwise, keeping the previous state as a standby step for receiving a bio-signal measurement command; and
(1-3) capturing a screen showing a selected ideal waveform among the waveforms displayed on the test result window and saving if a waveform selection command is received after each of steps 1-2-1 to 1-2-5, otherwise, keeping the measurement and displaying the measured waveforms continuously.

37. The cardiovascular analyzer of claim 36,
wherein analyzing waveforms from the received bio-signals and synthesizing the aortic arch internal pressure curve P from the analyzed waveforms in step 2 comprise:
(2-1) displaying an analysis menu window if an analysis command is received from the test and diagnosis window, otherwise, keeping the previous step;
(2-2) analyzing automatically feature points of the saved ECG, PCG and high frequency APG waveforms and displaying on the test result window if a systolic bio-signal analysis command is received from the analysis menu window, otherwise, keeping the previous step;
(2-3) analyzing automatically feature points of the saved ECG, PCG and low frequency APG waveforms and displaying on the test result window if a diastolic bio-signals analysis command is received from the analysis menu window, otherwise, keeping the previous step;
(2-4) displaying the saved left and right carotid artery waveforms on the test result window if a synthesized signal analysis command is received from the analysis menu window, otherwise, keeping the previous step;
(2-5) displaying enlarged waveforms analyzed in a selected interval on a lower left corner of the test result window if a detail analysis interval is selected in the left and right carotid artery waveforms showing on the test result window, otherwise, keeping the previous step; and
(2-6) displaying an aortic arch internal pressure curve, which is synthesized with the information including the saved ECG, PCG and APG waveforms, in a place clicked on the test results window if a vacant space of a lower right corner of the test results window is clicked after the sequential displays of the enlarged left and right carotid artery waveforms on the lower left corner of the test results window, otherwise, keeping the previous step.

38. The cardiovascular analyzer of claim 37,
wherein each of steps 2-2, 2-3, and 2-4 causes the main processing unit to return to step 1-1 if a test command is received from the result and diagnosis window after displaying each waveform on the test result window, and wherein if the test command is not received, each of steps 2-2, 2-3, and 2-4 is followed by the subsequent step.

39. The cardiovascular analyzer of claim 37,
wherein step 3 comprises:
(3-1) displaying a result menu window and a output device icon if a result display command is received from the test and diagnosis window, otherwise, displaying a patient list in the registered patient file on the test result window and receiving a signal for selecting a patient and new information of the selected patient till receiving a command;
(3-2) displaying a selected menu result if one is selected on the result menu window, otherwise, keeping step 3-1; and
(3-3) outputting the selected menu result if an output command is received from the output device icon after displaying the selected menu result, otherwise, keeping step 3-2.

40. The cardiovascular analyzer of claim 39,
wherein the result menu window comprises a Compliance-Resistance (C-R) chart; and
wherein the C-R chart is divided into sectors to show the coronary artery states according to the clinical results and
is dotted to show the states of the left and right coronary arteries of an examinee.

41. The cardiovascular analyzer of claim 17,
wherein step 3 further comprises:
calculating blood flow velocities $V_l$ and $V_r$ of the left and right coronary arteries from the aortic arch internal pressure curve P and the compliances $C_l$ and $C_r$ of the left and right coronary arteries and transmitting to the output unit.

42. The cardiovascular analyzer of claim 41,
wherein the blood flow velocities $V_l$ and $V_r$ of the left and right coronary arteries are calculated by the equations of:

the blood flow velocity $V_l$ of the left coronary artery is $$V_l = \frac{C_l}{A_0}\left(\frac{dp}{dt}\right)_{DW}$$

and the blood flow velocity $V_r$ of the right coronary artery is $$V_r = \frac{C_r}{A_0}\left(\frac{dp}{dt}\right)_{DW}$$

where $$\left(\frac{dp}{dt}\right)_{DW} = \frac{P(x_1, t_2) - P(x_1, t_1)}{t_2 - t_1}.$$

43. The cardiovascular analyzer of claim 42,
wherein analyzing waveforms from the received bio-signals in step 2 comprises:
finding feature points, including systolic upstroke point, systolic peak point, incisura point, diastolic peak point and diastolic end point, of the aortic arch internal pressure curve P by analyzing ECG signals and PCG signals measured by the ECG sensor and the PCG sensor of the bio-signals measurement system, respectively;
finding high frequency elements of the aortic arch internal pressure curve P by analyzing Cuff-APG pulse waves measured by a cuff pulse wave sensor, as one of the APG sensors of the bio-signals measurement system, which is pressurized above the systolic blood pressure;
finding low frequency elements of the aortic arch internal pressure curve P by analyzing Cuff-APG pulse waves measured by the cuff pulse wave sensor which is depressurized below the diastolic blood pressure; and
finding a time-frequency intensity of the aortic arch internal pressure curve P by analyzing APG pulse waves of the left and right carotid arteries measured by a carotid artery pulse wave sensor as one of the APG sensors of the bio-signals measurement system, and
wherein the synthesis of the aortic arch internal pressure curve P is based on basic information including the analyzed data of Cuff-APG pulse waves at the systole and the diastole and the analyzed data of APG pulse waves of the left and right carotid arteries.

44. The cardiovascular analyzer of claim 43,
wherein the main processing unit is further programmed to carry out the steps of:
displaying an initial screen including a search menu window, a patient information window, a test and diagnosis window and a test result window in the output unit before step 1;
receiving and saving the information of patient if a registration command for new patient is received in the initial screen, otherwise, receiving an opening command to open a registered patient file;
displaying a patient list in the registered patient file on the test result window if the opening command is received and receiving a signal for selecting a patient and new information of the selected patient, otherwise, displaying the initial screen continuously; and
displaying the information of new patient or the selected patient on the patient information window and receiving a test and diagnosis command, and
wherein the information of new patient or the selected patient comprises a personally identified information and body information including one or more of height, weight, blood pressure and race.

45. The cardiovascular analyzer of claim 44,
wherein performance of step 1 by the main processing unit further includes the steps of:
(1-1) displaying a command selection window for the bio-signal measurement if a test command is received from the test and diagnosis window, otherwise, keeping the previous state;
(1-2-1) receiving ECG, PCG and high frequency APG waveforms measured by the ECG sensor, the PCG sensor and a pressurized cuff pulse wave sensor as one of the APG sensors of the bio-signal measuring sensor unit and displaying on the test result window if the measurement command of a systolic pulse wave is received from the command selection window, otherwise, keeping the previous state as a standby step for receiving a bio-signal measurement command;
(1-2-2) receiving ECG, PCG and low frequency APG waveforms measured by the ECG sensor, the PCG sensor and a depressurized cuff pulse wave sensor as one of the APG sensors of the bio-signal measuring sensor unit and displaying on the test result window if the measurement command of a diastolic pulse wave is received from the command selection window, otherwise, keeping the previous state as a standby step for receiving a bio-signal measurement command;
(1-2-3) receiving ECG, PCG and left carotid artery APG waveforms measured by the ECG sensor, the PCG sensor and a carotid artery pulse wave sensor as one of the APG sensors of the bio-signal measuring sensor unit and displaying on the test result window if the measurement command of the left carotid artery is received from the command selection window, otherwise, keeping the previous state as a standby step for receiving a bio-signal measurement command;
(1-2-4) receiving ECG, PCG and right carotid artery APG waveforms measured by the ECG sensor, the PCG sensor and a carotid artery pulse wave sensor as one of the APG sensors of the bio-signal measuring sensor unit and displaying on the test result window if the measurement command of the right carotid artery is received from the command selection window, otherwise, keeping the previous state as a standby step for receiving a bio-signal measurement command;
(1-2-5) receiving ECG, PCG and femoral artery APG waveforms measured by the ECG sensor, the PCG sensor and a femoral artery pulse wave sensor as one of the APG sensors of the bio-signal measuring sensor unit and displaying on the test result window if the measurement command of the femoral artery is received from the command selection window, otherwise, keeping the previous state as a standby step for receiving a bio-signal measurement command; and
(1-3) capturing a screen showing a selected ideal waveform among the waveforms displayed on the test result window and saving if a waveform selection command is received after each of steps 1-2-1 to 1-2-5, otherwise, keeping the measurement and displaying the measured waveforms continuously.

46. The cardiovascular analyzer of claim 45,
wherein analyzing waveforms from the received bio-signals and synthesizing the aortic arch internal pressure curve P from the analyzed waveforms in step 2 comprise:
(2-1) displaying an analysis menu window if an analysis command is received from the test and diagnosis window, otherwise, keeping the previous step;
(2-2) analyzing automatically feature points of the saved ECG, PCG and high frequency APG waveforms and displaying on the test result window if a systolic bio-signal analysis command is received from the analysis menu window, otherwise, keeping the previous step;
(2-3) analyzing automatically feature points of the saved ECG, PCG and low frequency APG waveforms and displaying on the test result window if a diastolic bio-signals analysis command is received from the analysis menu window, otherwise, keeping the previous step;
(2-4) displaying the saved left and right carotid artery waveforms on the test result window if a synthesized signal analysis command is received from the analysis menu window, otherwise, keeping the previous step;
(2-5) displaying enlarged waveforms analyzed in a selected interval on a lower left corner of the test result window if a detail analysis interval is selected in the left and right carotid artery waveforms showing on the test result window, otherwise, keeping the previous step; and
(2-6) displaying an aortic arch internal pressure curve, which is synthesized with the information including the saved ECG, PCG and APG waveforms, in a place clicked on the test results window if a vacant space of a lower right corner of the test results window is clicked after the sequential displays of the enlarged left and right carotid artery waveforms on the lower left corner of the test results window, otherwise, keeping the previous step.

47. The cardiovascular analyzer of claim 46,
wherein each of steps 2-2, 2-3, and 2-4 causes the main processing unit to return to step 1-1 if a test command is received from the result and diagnosis window after displaying each waveform on the test result window, and wherein if the test command is not received, each of steps 2-2, 2-3, and 2-4 is followed by the subsequent step.

48. The cardiovascular analyzer of claim 46,
wherein step 3 comprises:
(3-1) displaying a result menu window and a output device icon if a result display command is received from the test and diagnosis window, otherwise, displaying a patient list in the registered patient file on the test result window and receiving a signal for selecting a patient and new information of the selected patient till receiving a command;
(3-2) displaying a selected menu result if one is selected on the result menu window, otherwise, keeping step 3-1; and
(3-3) outputting the selected menu result if an output command is received from the output device icon after displaying the selected menu result, otherwise, keeping step 3-2.

49. The cardiovascular analyzer of claim 48,
wherein the result menu window comprises a Compliance-Resistance (C-R) chart;
wherein the C-R chart is divided into sectors to show the coronary artery states according to the clinical results and is dotted to show the states of the left and right coronary arteries of an examinee.

50. The cardiovascular analyzer of claim 41,
wherein analyzing waveforms from the received bio-signals in step 2 comprises:
finding feature points, including systolic upstroke point, systolic peak point, incisura point, diastolic peak point and diastolic end point, of the aortic arch internal pressure curve P by analyzing ECG signals and PCG signals measured by the ECG sensor and the PCG sensor of the bio-signals measurement system, respectively;
finding high frequency elements of the aortic arch internal pressure curve P by analyzing Cuff-APG pulse waves measured by a cuff pulse wave sensor, as one of the APG sensors of the bio-signals measurement system, which is pressurized above the systolic blood pressure;
finding low frequency elements of the aortic arch internal pressure curve P by analyzing Cuff-APG pulse waves measured by the cuff pulse wave sensor which is depressurized below the diastolic blood pressure; and
finding a time-frequency intensity of the aortic arch internal pressure curve P by analyzing APG pulse waves of the left and right carotid arteries measured by a carotid artery pulse wave sensor as one of the APG sensors of the bio-signals measurement system, and
wherein the synthesis of the aortic arch internal pressure curve P is based on basic information including the analyzed data of Cuff-APG pulse waves at the systole and the diastole and the analyzed data of APG pulse waves of the left and right carotid arteries.

51. The cardiovascular analyzer of claim 50,
wherein the main processing unit is further programmed to carry out the steps of:
displaying an initial screen including a search menu window, a patient information window, a test and diagnosis window and a test result window in the output unit before step 1;
receiving and saving the information of patient if a registration command for new patient is received in the initial screen, otherwise, receiving an opening command to open a registered patient file;
displaying a patient list in the registered patient file on the test result window if the opening command is received and receiving a signal for selecting a patient and new information of the selected patient, otherwise, displaying the initial screen continuously; and
displaying the information of new patient or the selected patient on the patient information window and receiving a test and diagnosis command, and
wherein the information of new patient or the selected patient comprises a personally identified information and body information including one or more of height, weight, blood pressure and race.

52. The cardiovascular analyzer of claim 51,
wherein performance of step 1 by the main processing unit further includes the steps of:
(1-1) displaying a command selection window for the bio-signal measurement if a test command is received from the test and diagnosis window, otherwise, keeping the previous state;
(1-2-1) receiving ECG, PCG and high frequency APG waveforms measured by the ECG sensor, the PCG sensor and a pressurized cuff pulse wave sensor as one of the APG sensors of the bio-signal measuring sensor unit and displaying on the test result window if the measurement command of a systolic pulse wave is received from the command selection window, otherwise, keeping the previous state as a standby step for receiving a bio-signal measurement command;

(1-2-2) receiving ECG, PCG and low frequency APG waveforms measured by the ECG sensor, the PCG sensor and a depressurized cuff pulse wave sensor as one of the APG sensors of the bio-signal measuring sensor unit and displaying on the test result window if the measurement command of a diastolic pulse wave is received from the command selection window, otherwise, keeping the previous state as a standby step for receiving a bio-signal measurement command;

(1-2-3) receiving ECG, PCG and left carotid artery APG waveforms measured by the ECG sensor, the PCG sensor and a carotid artery pulse wave sensor as one of the APG sensors of the bio-signal measuring sensor unit and displaying on the test result window if the measurement command of the left carotid artery is received from the command selection window, otherwise, keeping the previous state as a standby step for receiving a bio-signal measurement command;

(1-2-4) receiving ECG, PCG and right carotid artery APG waveforms measured by the ECG sensor, the PCG sensor and a carotid artery pulse wave sensor as one of the APG sensors of the bio-signal measuring sensor unit and displaying on the test result window if the measurement command of the right carotid artery is received from the command selection window, otherwise, keeping the previous state as a standby step for receiving a bio-signal measurement command;

(1-2-5) receiving ECG, PCG and femoral artery APG waveforms measured by the ECG sensor, the PCG sensor and a femoral artery pulse wave sensor as one of the APG sensors of the bio-signal measuring sensor unit and displaying on the test result window if the measurement command of the femoral artery is received from the command selection window, otherwise, keeping the previous state as a standby step for receiving a bio-signal measurement command; and (1-3) capturing a screen showing a selected ideal waveform among the waveforms displayed on the test result window and saving if a waveform selection command is received after each of steps 1-2-1 to 1-2-5, otherwise, keeping the measurement and displaying the measured waveforms continuously.

53. The cardiovascular analyzer of claim 52, wherein analyzing waveforms from the received bio-signals and synthesizing the aortic arch internal pressure curve P from the analyzed waveforms in step 2 comprise:

(2-1) displaying an analysis menu window if an analysis command is received from the test and diagnosis window, otherwise, keeping the previous step;

(2-2) analyzing automatically feature points of the saved ECG, PCG and high frequency APG waveforms and displaying on the test result window if a systolic bio-signal analysis command is received from the analysis menu window, otherwise, keeping the previous step;

(2-3) analyzing automatically feature points of the saved ECG, PCG and low frequency APG waveforms and displaying on the test result window if a diastolic bio-signals analysis command is received from the analysis menu window, otherwise, keeping the previous step;

(2-4) displaying the saved left and right carotid artery waveforms on the test result window if a synthesized signal analysis command is received from the analysis menu window, otherwise, keeping the previous step;

(2-5) displaying enlarged waveforms analyzed in a selected interval on a lower left corner of the test result window if a detail analysis interval is selected in the left and right carotid artery waveforms showing on the test result window, otherwise, keeping the previous step; and (2-6) displaying an aortic arch internal pressure curve, which is synthesized with the information including the saved ECG, PCG and APG waveforms, in a place clicked on the test results window if a vacant space of a lower right corner of the test results window is clicked after the sequential displays of the enlarged left and right carotid artery waveforms on the lower left corner of the test results window, otherwise, keeping the previous step.

54. The cardiovascular analyzer of claim 53, wherein each of steps 2-2, 2-3, and 2-4 causes the main processing unit to return to step 1-1 if a test command is received from the result and diagnosis window after displaying each waveform on the test result window, and wherein if the test command is not received, each of steps 2-2, 2-3, and 2-4 is followed by the subsequent step.

55. The cardiovascular analyzer of claim 53, wherein step 3 comprises:

(3-1) displaying a result menu window and a output device icon if a result display command is received from the test and diagnosis window, otherwise, displaying a patient list in the registered patient file on the test result window and receiving a signal for selecting a patient and new information of the selected patient till receiving a command;

(3-2) displaying a selected menu result if one is selected on the result menu window, otherwise, keeping step 3-1; and (3-3) outputting the selected menu result if an output command is received from the output device icon after displaying the selected menu result, otherwise, keeping step 3-2.

56. The cardiovascular analyzer of claim 55, wherein the result menu window comprises a Compliance-Resistance (C-R) chart; and wherein the C-R chart is divided into sectors to show the coronary artery states according to the clinical results and is dotted to show the states of the left and right coronary arteries of an examinee.

57. The cardiovascular analyzer of claim 17, wherein the blood flow volumes $S_l$ and $S_r$, the compliances $C_l$ and $C_r$, and the blood flow resistances $R_l$ and $R_r$ of the left and right coronary arteries are calculated by the equations of:

the blood flow volume $S_l$ of the left coronary artery is $$S_l = KA_d\left(\frac{t_* + \Delta t_d}{\Delta t_d}\right),$$

the blood flow volume $S_r$ of the right coronary artery is $$S_r = K_1 pR^2(1-v^2)^{1/2}Pm(1+Ad/K_2As)/(\rho a),$$

the compliance $C_l$ of the left coronary artery is $$C_l = \frac{\left(S_l - \frac{A_d}{R_l}\right)}{(P_* - P_d)},$$

the compliance $C_r$ of the right coronary artery is $$C_r = \frac{k_2 A_S - A_d}{P_S^* - P_d} \cdot \frac{S_r}{k_2 A_S + A_d},$$

the blood flow resistances $R_{l1}$ and $R_{l2}$ of the left coronary artery are $$R_{l_1} = \frac{P_d - P_v}{S_l}$$

and $$R_{l_2} = \frac{\overline{P}}{S_v},$$

and
the blood flow resistance $R_r$ of right coronary artery is $$Rr = \frac{k_2 A_S + A_d}{Sr}$$

where Ad is an area of the aortic arch internal pressure curve P at diastole, As is an area of the aortic arch internal pressure curve P at systole, t* is a time to a point which the first-order derivative function of the aortic arch internal pressure curve P is zero at systole, υ is Poisson constant of blood vessel, R is an equivalent radius of blood vessel, Pm is an average blood pressure, ρ is a blood density, a is a propagation velocity of pulse wave, Pd is a blood pressure of the aortic arch internal pressure curve P at diastole, Ps is a blood pressure of the aortic arch internal pressure curve P at systole, P* and Ps* are blood pressure of the aortic arch internal pressure curve P at an incisura point, $P_v$ is a blood pressure of the left coronary artery at random point, $S_v$ is a cardiac output, and K, $K_1$ and $K_2$ are coefficients.

58. The cardiovascular analyzer of claim 57,
wherein analyzing waveforms from the received bio-signals in step 2 comprises:
finding feature points, including systolic upstroke point, systolic peak point, incisura point, diastolic peak point and diastolic end point, of the aortic arch internal pressure curve P by analyzing ECG signals and PCG signals measured by the ECG sensor and the PCG sensor of the bio-signals measurement system, respectively;
finding high frequency elements of the aortic arch internal pressure curve P by analyzing Cuff-APG pulse waves measured by a cuff pulse wave sensor, as one of the APG sensors of the bio-signals measurement system, which is pressurized above the systolic blood pressure;
finding low frequency elements of the aortic arch internal pressure curve P by analyzing Cuff-APG pulse waves measured by the cuff pulse wave sensor which is depressurized below the diastolic blood pressure; and
finding a time-frequency intensity of the aortic arch internal pressure curve P by analyzing APG pulse waves of the left and right carotid arteries measured by a carotid artery pulse wave sensor as one of the APG sensors of the bio-signals measurement system, and
wherein the synthesis of the aortic arch internal pressure curve P is based on basic information including the analyzed data of Cuff-APG pulse waves at the systole and the diastole and the analyzed data of APG pulse waves of the left and right carotid arteries.

59. The cardiovascular analyzer of claim 58,
wherein the main processing unit is further programmed to carry out the steps of:
displaying an initial screen including a search menu window, a patient information window, a test and diagnosis window and a test result window in the output unit before step 1;
receiving and saving the information of patient if a registration command for new patient is received in the initial screen, otherwise, receiving an opening command to open a registered patient file;
displaying a patient list in the registered patient file on the test result window if the opening command is received and receiving a signal for selecting a patient and new information of the selected patient, otherwise, displaying the initial screen continuously; and
displaying the information of new patient or the selected patient on the patient information window and receiving a test and diagnosis command, and
wherein the information of new patient or the selected patient comprises a personally identified information and body information including one or more of height, weight, blood pressure and race.

60. The cardiovascular analyzer of claim 59,
wherein performance of step 1 by the main processing unit further includes the steps of
(1-1) displaying a command selection window for the bio-signal measurement if a test command is received from the test and diagnosis window, otherwise, keeping the previous state;
(1-2-1) receiving ECG, PCG and high frequency APG waveforms measured by the ECG sensor, the PCG sensor and a pressurized cuff pulse wave sensor as one of the APG sensors of the bio-signal measuring sensor unit and displaying on the test result window if the measurement command of a systolic pulse wave is received from the command selection window, otherwise, keeping the previous state as a standby step for receiving a bio-signal measurement command;
(1-2-2) receiving ECG, PCG and low frequency APG waveforms measured by the ECG sensor, the PCG sensor and a depressurized cuff pulse wave sensor as one of the APG sensors of the bio-signal measuring sensor unit and displaying on the test result window if the measurement command of a diastolic pulse wave is received from the command selection window, otherwise, keeping the previous state as a standby step for receiving a bio-signal measurement command;
(1-2-3) receiving ECG, PCG and left carotid artery APG waveforms measured by the ECG sensor, the PCG sensor and a carotid artery pulse wave sensor as one of the APG sensors of the bio-signal measuring sensor unit and displaying on the test result window if the measurement command of the left carotid artery is received from the command selection window, otherwise, keeping the previous state as a standby step for receiving a bio-signal measurement command;

(1-2-4) receiving ECG, PCG and right carotid artery APG waveforms measured by the ECG sensor, the PCG sensor and a carotid artery pulse wave sensor as one of the APG sensors of the bio-signal measuring sensor unit and displaying on the test result window if the measurement command of the right carotid artery is received from the command selection window, otherwise, keeping the previous state as a standby step for receiving a bio-signal measurement command;

(1-2-5) receiving ECG, PCG and femoral artery APG waveforms measured by the ECG sensor, the PCG sensor and a femoral artery pulse wave sensor as one of the APG sensors of the bio-signal measuring sensor unit and displaying on the test result window if the measurement command of the femoral artery is received from the command selection window, otherwise, keeping the previous state as a standby step for receiving a bio-signal measurement command; and (1-3) capturing a screen showing a selected ideal waveform among the waveforms displayed on the test result window and saving if a waveform selection command is received after each of steps 1-2-1 to 1-2-5, otherwise, keeping the measurement and displaying the measured waveforms continuously.

61. The cardiovascular analyzer of claim 60,
wherein analyzing waveforms from the received bio-signals and synthesizing the aortic arch internal pressure curve P from the analyzed waveforms in step 2 comprise:

(2-1) displaying an analysis menu window if an analysis command is received from the test and diagnosis window, otherwise, keeping the previous step;

(2-2) analyzing automatically feature points of the saved ECG, PCG and high frequency APG waveforms and displaying on the test result window if a systolic bio-signal analysis command is received from the analysis menu window, otherwise, keeping the previous step;

(2-3) analyzing automatically feature points of the saved ECG, PCG and low frequency APG waveforms and displaying on the test result window if a diastolic bio-signals analysis command is received from the analysis menu window, otherwise, keeping the previous step;

(2-4) displaying the saved left and right carotid artery waveforms on the test result window if a synthesized signal analysis command is received from the analysis menu window, otherwise, keeping the previous step;

(2-5) displaying enlarged waveforms analyzed in a selected interval on a lower left corner of the test result window if a detail analysis interval is selected in the left and right carotid artery waveforms showing on the test result window, otherwise, keeping the previous step; and (2-6) displaying an aortic arch internal pressure curve, which is synthesized with the information including the saved ECG, PCG and APG waveforms, in a place clicked on the test results window if a vacant space of a lower right corner of the test results window is clicked after the sequential displays of the enlarged left and right carotid artery waveforms on the lower left corner of the test results window, otherwise, keeping the previous step.

62. The cardiovascular analyzer of claim 61,
wherein each of steps 2-2, 2-3, and 2-4 causes the main processing unit to return to step 1-1 if a test command is received from the result and diagnosis window after displaying each waveform on the test result window, and wherein if the test command is not received, each of steps 2-2, 2-3, and 2-4 is followed by the subsequent step.

63. The cardiovascular analyzer of claim 61,
wherein step 3 comprises:
(3-1) displaying a result menu window and a output device icon if a result display command is received from the test and diagnosis window, otherwise, displaying a patient list in the registered patient file on the test result window and receiving a signal for selecting a patient and new information of the selected patient till receiving a command;

(3-2) displaying a selected menu result if one is selected on the result menu window, otherwise, keeping step 3-1; and (3-3) outputting the selected menu result if an output command is received from the output device icon after displaying the selected menu result, otherwise, keeping step 3-2.

64. The cardiovascular analyzer of claim 63,
wherein the result menu window comprises a Compliance-Resistance (C-R) chart; and
wherein the C-R chart is divided into sectors to show the coronary artery states according to the clinical results and
is dotted to show the states of the left and right coronary arteries of an examinee.

65. The cardiovascular analyzer of claim 57,
wherein the coefficient $K_1$ is related to a blood flow volume flowing from an entrance of the coronary artery to the right coronary artery and is 0.12~0.15;
wherein the coefficient $K_2$ is a tissue internal pressure coefficient and is 0.7~0.75; and
wherein the coefficient K is calculated by $$K = kA \cdot \sqrt{C_s}$$
$$= kA\left[(2mP_d + 1) \cdot \frac{\frac{A_d}{R} - n(P_*^2 - P_d^2)}{(P_* - P_d) + m(P_*^2 - P_d^2)} + 2nP_d\right]$$

where k is a coefficient related to a blood flow volume flowing from an entrance of the coronary artery to the left coronary artery and is 0.85~0.88, $A=\pi R^2$ is an equivalent area of the left coronary artery, $C_s$ is a compliance at systole, and m and n are Cope constants.

66. The cardiovascular analyzer of claim 65,
wherein analyzing waveforms from the received bio-signals in step 2 comprises:
finding feature points, including systolic upstroke point, systolic peak point, incisura point, diastolic peak point and diastolic end point, of the aortic arch internal pressure curve P by analyzing ECG signals and PCG signals measured by the ECG sensor and the PCG sensor of the bio-signals measurement system, respectively;
finding high frequency elements of the aortic arch internal pressure curve P by analyzing Cuff-APG pulse waves measured by a cuff pulse wave sensor, as one of the APG sensors of the bio-signals measurement system, which is pressurized above the systolic blood pressure;
finding low frequency elements of the aortic arch internal pressure curve P by analyzing Cuff-APG pulse waves measured by the cuff pulse wave sensor which is depressurized below the diastolic blood pressure; and finding a time-frequency intensity of the aortic arch internal pressure curve P by analyzing APG pulse waves of the left and right carotid arteries measured by a carotid artery pulse wave sensor as one of the APG sensors of the bio-signals measurement system, and wherein the synthesis of the aortic arch internal pressure curve P is based on basic information including the analyzed data of Cuff-APG pulse waves at the systole and the diastole and the analyzed data of APG pulse waves of the left and right carotid arteries.

67. The cardiovascular analyzer of claim 66,
wherein the main processing unit is further programmed to carry out the steps of:
displaying an initial screen including a search menu window, a patient information window, a test and diagnosis window and a test result window in the output unit before step 1;
receiving and saving the information of patient if a registration command for new patient is received in the initial screen, otherwise, receiving an opening command to open a registered patient file;
displaying a patient list in the registered patient file on the test result window if the opening command is received and receiving a signal for selecting a patient and new information of the selected patient, otherwise, displaying the initial screen continuously; and
displaying the information of new patient or the selected patient on the patient information window and receiving a test and diagnosis command, and
wherein the information of new patient or the selected patient comprises a personally identified information and body information including one or more of height, weight, blood pressure and race.

68. The cardiovascular analyzer of claim 67,
wherein performance of step 1 by the main processing unit further includes the steps of:
(1-1) displaying a command selection window for the bio-signal measurement if a test command is received from the test and diagnosis window, otherwise, keeping the previous state;
(1-2-1) receiving ECG, PCG and high frequency APG waveforms measured by the ECG sensor, the PCG sensor and a pressurized cuff pulse wave sensor as one of the APG sensors of the bio-signal measuring sensor unit and displaying on the test result window if the measurement command of a systolic pulse wave is received from the command selection window, otherwise, keeping the previous state as a standby step for receiving a bio-signal measurement command;
(1-2-2) receiving ECG, PCG and low frequency APG waveforms measured by the ECG sensor, the PCG sensor and a depressurized cuff pulse wave sensor as one of the APG sensors of the bio-signal measuring sensor unit and displaying on the test result window if the measurement command of a diastolic pulse wave is received from the command selection window, otherwise, keeping the previous state as a standby step for receiving a bio-signal measurement command;
(1-2-3) receiving ECG, PCG and left carotid artery APG waveforms measured by the ECG sensor, the PCG sensor and a carotid artery pulse wave sensor as one of the APG sensors of the bio-signal measuring sensor unit and displaying on the test result window if the measurement command of the left carotid artery is received from the command selection window, otherwise, keeping the previous state as a standby step for receiving a bio-signal measurement command;
(1-2-4) receiving ECG, PCG and right carotid artery APG waveforms measured by the ECG sensor, the PCG sensor and a carotid artery pulse wave sensor as one of the APG sensors of the bio-signal measuring sensor unit and displaying on the test result window if the measurement command of the right carotid artery is received from the command selection window, otherwise, keeping the previous state as a standby step for receiving a bio-signal measurement command;
(1-2-5) receiving ECG, PCG and femoral artery APG waveforms measured by the ECG sensor, the PCG sensor and a femoral artery pulse wave sensor as one of the APG sensors of the bio-signal measuring sensor unit and displaying on the test result window if the measurement command of the femoral artery is received from the command selection window, otherwise, keeping the previous state as a standby step for receiving a bio-signal measurement command; and
(1-3) capturing a screen showing a selected ideal waveform among the waveforms displayed on the test result window and saving if a waveform selection command is received after each of steps 1-2-1 to 1-2-5, otherwise, keeping the measurement and displaying the measured waveforms continuously.

69. The cardiovascular analyzer of claim 68,
wherein analyzing waveforms from the received bio-signals and synthesizing the aortic arch internal pressure curve P from the analyzed waveforms in step 2 comprise:
(2-1) displaying an analysis menu window if an analysis command is received from the test and diagnosis window, otherwise, keeping the previous step;
(2-2) analyzing automatically feature points of the saved ECG, PCG and high frequency APG waveforms and displaying on the test result window if a systolic bio-signal analysis command is received from the analysis menu window, otherwise, keeping the previous step;
(2-3) analyzing automatically feature points of the saved ECG, PCG and low frequency APG waveforms and displaying on the test result window if a diastolic bio-signals analysis command is received from the analysis menu window, otherwise, keeping the previous step;
(2-4) displaying the saved left and right carotid artery waveforms on the test result window if a synthesized signal analysis command is received from the analysis menu window, otherwise, keeping the previous step;
(2-5) displaying enlarged waveforms analyzed in a selected interval on a lower left corner of the test result window if a detail analysis interval is selected in the left and right carotid artery waveforms showing on the test result window, otherwise, keeping the previous step; and
(2-6) displaying an aortic arch internal pressure curve, which is synthesized with the information including the saved ECG, PCG and APG waveforms, in a place clicked on the test results window if a vacant space of a lower right corner of the test results window is clicked after the sequential displays of the enlarged left and right carotid artery waveforms on the lower left corner of the test results window, otherwise, keeping the previous step.

70. The cardiovascular analyzer of claim 69,
wherein each of steps 2-2, 2-3, and 2-4 causes the main processing unit to return to step 1-1 if a test command is received from the result and diagnosis window after displaying each waveform on the test result window, and wherein if the test command is not received, each of steps 2-2, 2-3, and 2-4 is followed by the subsequent step.

71. The cardiovascular analyzer of claim 69,
wherein step 3 comprises:
(3-1) displaying a result menu window and a output device icon if a result display command is received from the test and diagnosis window, otherwise, displaying a patient list in the registered patient file on the test result window and receiving a signal for selecting a patient and new information of the selected patient till receiving a command;
(3-2) displaying a selected menu result if one is selected on the result menu window, otherwise, keeping step 3-1; and
(3-3) outputting the selected menu result if an output command is received from the output device icon after displaying the selected menu result, otherwise, keeping step 3-2.

72. The cardiovascular analyzer of claim 71,
wherein the result menu window comprises a Compliance-Resistance (C-R) chart;
wherein the C-R chart is divided into sectors to show the coronary artery states according to the clinical results and
is dotted to show the states of the left and right coronary arteries of an examinee.

\* \* \* \* \*